Figure 1:
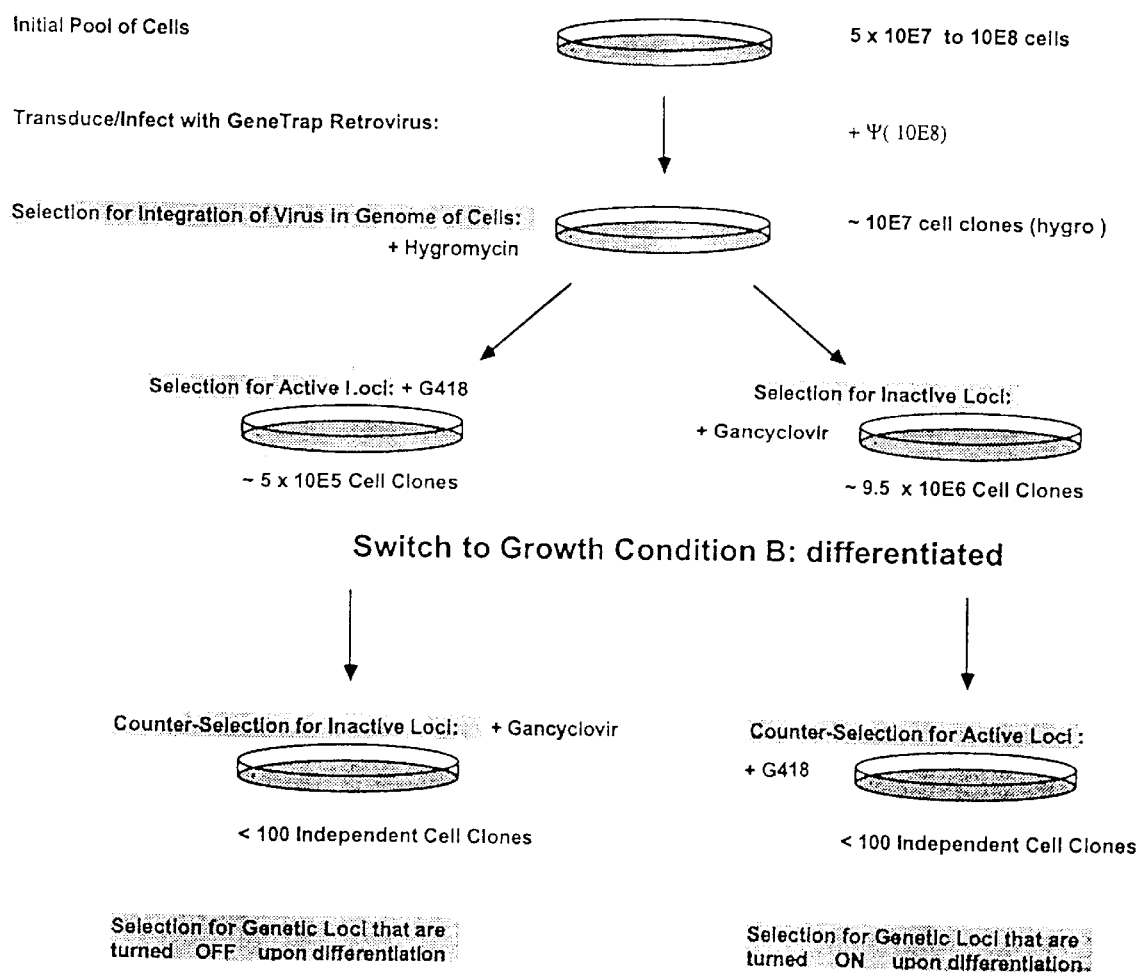

United States Patent [19]
Baetscher et al.

[11] Patent Number: 5,922,601
[45] Date of Patent: *Jul. 13, 1999

[54] HIGH EFFICIENCY GENE TRAP SELECTION OF REGULATED GENETIC LOCI

[75] Inventors: Manfred Baetscher, Winchester; Waan-Jeng Nir, Reading, both of Mass.

[73] Assignee: BioTransplant, Inc., Charlestown, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/716,854

[22] Filed: Sep. 16, 1996

Related U.S. Application Data

[63] Continuation of application No. 08/374,833, Jan. 19, 1995, abandoned.

[51] Int. Cl.$^6$ .............. C12N 15/64; C12N 5/10; C12N 15/11; C12N 15/79
[52] U.S. Cl. .............. 435/456; 435/4; 435/6; 435/320.1; 435/325; 536/23.1; 536/23.4; 536/24.1
[58] Field of Search ............ 536/23.1, 23.4, 536/24.1; 435/320.1, 172.3, 325, 4, 6

[56] References Cited

PUBLICATIONS

Sugimoto et al. 1994. Efficient Expression of Drug–Selectable Genes in Retroviral Vectors Under Control of an Internal Ribosome Entry Site. Bio/technology, 12:694–698.

Alberts et al. 1989. Molecular Biology of The Cell, 2$^{nd}$ edn. Garland Publishing Inc., New York, p. 533.

Casadaban, M.J., and Cohen, S.N. (1979). Lactose genses fused to exogenous prometers in one step using a Mulac bacteriophage: In vivo probe for transcriptional control sequences. Proc. Natl. Acad. Sci. USA 76, 4530–4533.

Chang, W., Hubbard, S.C., Friedel, C., and Ruley, H.E. (1993). Enrichment of insertional mutants following retrovirus gene trap selection. Virology 193, 737–747.

Chu, G., and Sharp, P.A. (1981). A gene chimaera of SV40 and mouse β–globin is transcribed and properly spliced. Nature 289, 378–382.

DeGregori, J., et al., e. (1994). A murine homolog of the yeast RNA 1 gene is required for postimplantation development. Genes & Development 8, 265–276.

Freidrich, G., and Soraino, P. (1991). Promoter traps in embryonic stem cells; a genetic screen to identify and mutate developmental genes in mice. Genes & Development 5, 1513–1523.

Gossler, A., Joyner, A.L., Rossant, J., and Skarnes, W.C. (1989). Mouse embryonic stem cells and reporter constructs to detect developmentally regulated genes. Science 244.

Hill, D.P., and Wurst, W. (1993). Screening for novel pattern formation genes using gene trap approaches. Methods in Enzymology 225, 664–681.

(List continued on next page.)

Primary Examiner—Johnny F. Railey, II
Attorney, Agent, or Firm—Elliot M. Olstein; Raina Semionow

[57] ABSTRACT

A gene trap construct for identification of genes whose activity is regulated upon a cellular transition event which comprises in downstream sequence (i) a cassette having a functional splice acceptor, a translation stop sequence and an internal ribosome entry site and (ii) a promoterless protein coding sequence encoding at least one polypeptide providing positive and negative selection traits. A method for identification of genes whose activity is regulated upon a cellular transition event by introducing the gene trap construct into a cell and observing expression of the positive and/or negative selection traits before and after the transition event.

31 Claims, 8 Drawing Sheets

OTHER PUBLICATIONS

Joyner, A.L. (1991). Gene targeting and gene trap screens using embryonic stem cells; new approaches to mammalian development. BioEssays 13, 649–656.

Joyner, A.L., Auerbach, A., and Skarnes. W.C. (1992). The gene trap approach in embryonic stem cells: the potential for genetic screens in mice. Ciba Foundation Symposium 165, 277–288.

Macleod, D., Lovell–Badge, R., Jones, S. and Jackson, I. (1991). A promoter trap in embryonic stem (ES) cells selects for integration of DNA into CpG islands. Nucleic Acids Research 19, 17–23.

Mountford, P., Zevnik, B., Duwel, A., Nichols, J. Li, M., Dani, C., Robertson, M., Chambers, I., and Smith, A. (1994). Dicistronic targeting constructs: reporters and modifiers of mammalian gene expression. Proc.Natl.Acad.Sci.U.S.A. 91, 4303–4307.

Reddy, S., DeGregori, J.V., von Melchner, H., and Ruley, H.E. (1991). Retrovirus promoter–trap vector to induce lacZ gene fusions in mammalian cells. Journal of Virology 65, 1507–1515.

Reddy, S., Rayburn, H., von Melchner, H., and Ruley, H.E. (1992). Fluorescence–activated sorting of totipotent embryonic stem cells expressing developmentally regulated lacZ fusion genes. Proc. Natl. Acad. Sci. USA 89, 6721–6725.

Skarnes, W.C., Auerbach, B.A., and Joyner, A.L. (1992). A gene trap approach in mouse embryonic stem cells: the lacZ reporter is activated by splicing, reflects endogenous gene expression, and is mutagenic in mice. Genes & Development 6, 903–918.

Soriano, P., Friedrich G., and Lawinger, P. (1991). Promoter interactions in retrovirus vectors introduced into fibroblasts and embryonic stem cells. Journal of Virology 65, (5), 2314–2319.

Vaulont, S., Daines, S., and Evans, M. (1995). Disruption of the adenosine deaminase (ADA) gene using a dicistronic promoterless construct: production of an ADA–deficient homozygote ES cell line. Transgenic Research 4, 247–255.

Von Melchner, H., DeGregori, J.V., Rayburn, H., Reddy, S., Friedel, C., and Ruley, H.E. (1992). Selective disruption of genes expressed in totipotent embryonal stem cells. Genes & Development 6, 919–927.

Von Melchner, H., Reddy, S., and Ruley, H.E. (1990). Isolation of cellular promoters by using a retrovirus promoter trap. Proc. Natl. Acad. Sci. USA 87, 3733–3737.

Weber, R., de Villiers, J., and Schaffner, W. (1984). An SV40 "enhancer trap" incorporates exogenous enhancers or generates enhancers from its own sequences. Cell 36, 983–992.

Genetic Selection of Regulated Genes
(Flow Chart)

HIGH EFFICIENCY GENE TRAP SELECTION OF REGULATED GENETIC LOCI

This application is a continuation of application Ser. No. 08/374,833, filed Jan. 19, 1995, now abandoned.

This invention relates to gene trap vectors that include promoterless dominant reporter genes suitable for both positive and negative selection. Expression of reporter gene activity is independent of the reading frame of the trapped cellular gene which allows for high efficiency selection and cloning of regulated chromosomal loci. The invention provides a method to establish a profile of genes that are regulated in response to physiological processes such as embryonic development and cellular differentiation as well as in pathological processes, including tumorigenic transformation and autoimmune disorders.

Regulation of gene expression is pivotal to our understanding of biological processes, including embryogenesis and the differentiation of pluripotent progenitor cells (McGinnis and Krumlauf, 1992 ; Krumlauf, 1992; Malicki et al., 1990), and abnormalities in the control of these regulatory mechanisms are causal to many pathological processes including cancer (Hunter, 1991; Varmus,1984) and autoimmune disorders (Fowell, 1991; Watanabe-Fukunaga, 1992) . Extensive research efforts have been directed to the identification and characterization of genes specifically associated with physiological and/or pathological processes of human disease, as well as for the development of relevant animal models. However, tools suitable to identify regulated genes as well as to monitor the activity of genetic loci are limited.

Gene regulation involves a series of enzymatic processes that control encoding of genetic information on DNA into biologically active gene products. The initial intermediate between DNA and the active gene product is the pre-messenger RNA (pre-mRNA) or heterogeneous nuclear RNA (hnRNA) generated during transcription by the DNA-dependent RNA polymerase type II (Young, 1991; Brown, 1984). Generation of active gene products including peptides and proteins requires hnRNA to be processed into mature biologically active MRNA. To summarize, processing and transport of pre-mRNA includes mechanisms such as capping of the 5'-end, splicing of introns at intron/exon junctions and polyadenylation of the 3'- end that permit proper transport of mRNA from the nucleus to the cytoplasm for translation on polysomes (Sharp, 1987; Weiner, 1993)

With very few exceptions, eukaryotic genes consist of protein coding sequences interrupted by sequences that do not code for protein, but are included in the primary transcript or pre messenger RNA. These non-coding sequences, or introns, are removed during RNA splicing, whereby the 3'-splice junction of the upstream protein coding region (exon) is joined with the 5'-splice junction of the nearest downstream exon. Correspondingly, the 3' and 5'-splice junctions on an exon are called the "splice donor" and "splice acceptor", respectively (Sharp, 1987; Padgett et al. 1985) For the most part, the linear organization of exons is faithfully reproduced on the spliced RNA. Some genes, however, are more complex and can give rise to several gene products generated by alternative splicing, whereby certain exons are deliberately excluded or skipped in some cell types but not in others. The rationale for that feature can be explained by the fact that exons often code for discrete structural protein domains with distinct functional properties. A gene that is made up of many exons can thus give rise to many gene products by shuffling exons as functional modules. Nature clearly strives for maximizing functional diversity with limited structural components. For example, the gene encoding the mouse steel factor can code either for a membrane bound receptor or a soluble molecule depending on whether or not exon 6 is included, which encodes a protease cleavage site to release the extracellular domains (Flanagan et al, 1991). The detailed biochemical mechanisms that regulate alternative splicing are still unclear, but there is evidence that certain conserved consensus sequences located around the splice acceptor and splice donor sites are essential (Guthrie, 1991)

The process of RNA splicing, taken together with the information that exons can be shuffled as discrete functional modules, has been exploited by inserting molecular tags resembling exons at random locations in the genome. Provided that this tag resembling an exon is a promoterless reporter gene, expression of the reporter is dependent on cellular promoters and implies that the tag jumped into an active chromosomal locus. The size of the human genome as well as those of most other mammals is in the range of $3 \times 10^9$ base pairs. The currently estimated maximal number of genes within a mammalian genome is in the order of around 100,000. Of the genes identified thus far and analyzed, the average size is 16.6 kb, of which 2.2 kb is the average size of the mature MRNA (Sulston, 1992). Thus, intron sequences which are non-coding make up the vast majority of the size of genes (~87%) and are the likely sites of integration of molecular tags that integrate at random (Casadaban and Cohen 1980; Chu and Sharp 1981; Weber at al 1984). Tags basically consists of a promoterless reporter gene linked to exogenous functional splice acceptors. For example, Gossler et al. (1989) used the bacterial β-galactosidase gene as a reporter engineered downstream of the splice acceptor consensus sequence derived from the mouse engrailed locus. Introduction of this splice acceptor-reporter construction into mouse embryonic stem (ES) cells was performed to identify genes that were active in ES cells. Upon introduction of ES cells expressing the reporter gene into recipient embryos to generate chimeras, expression of the reporter gene gave information as to the temporal and spatial pattern of expression of the locus of integration (Gossler et al, 1989). Another, more advanced, type of gene trap consisted of a fusion protein including the β-galactosidase and the neomycin phosphotransferase gene. This fusion protein gene was linked to the adenovirus splice acceptor and was successfully used to trap loci in ES cells that turned out to be developmentally regulated when checked in the whole animal (Friedrich and Soriano, 1991), While such gene traps have been used to identify active chromosomal loci, their application has been limited to ES cells used to study the pattern of expression of trapped loci in the whole animal.

A different design of a promoter trap included packaging into retroviruses for more efficient delivery into cells. One type of retroviral enhancer trap was described by vonMelchner et al. (Genes Dev. 1992; U.S. Pat. # 5,364,783). The basic design of this vector includes a reporter protein coding sequence engineered into the U3 portion of the 3' LTR. No splice acceptor consensus sequences are included, limiting its utility to work as an enhancer trap only. A different approach to a gene trap using retroviral vectors was pursued by Friedrich and Soriano (Genes Dev. 1991), who engineered a lacZ-neo fusion protein linked to a splicing acceptor. LacZ-neo fusion protein expression from trapped loci allows not only for drug selection, but also for visualization of β-galatactosidase expression using the chromogenic substrate, X-gal. Packaged in a retroviral vector, this trap can be delivered efficiently into target cells. Specifically, the pGen- (Soriano et al. 1991) vector, derived from the Moloney murine leukemia virus (MoMLV), was used in reverse orientation to avoid interference of the transcriptionally active viral 5' LTR with the trap construction. This design provided advantages over previous types of gene traps by eliminating adverse effects of the retroviral LTRs on the trap function. This made it possible to generate a large number of trapped genes in ES cells that could then be studied in the context of the whole animal.

A considerable advantage of retroviral trap-delivery systems over standard transfection protocols concerns not only the efficiency of delivering the trap, but also the mode of integration of trap vector into the host genome. While standard transfections using linear or supercoiled plasmid DNA can cause genomic rearrangements at the locus of integration, possibly causing adverse effects, retroviruses usually integrate into the genome without causing such rearrangements (Miller and Rosman, 1989).

Thus, the general concept of tagging active loci by random integration of retroviral vectors containing a splice acceptor-reporter insert appeared promising. However, current vectors have had limited application. These vectors permit studies on trapped genes in the entire animal, rather than more generally in homogeneous or heterogeneous populations of cells in vivo or in vitro. A trap design that allows for selection of cell populations in which a trapped locus is either active or inactive would have a much broader range of applications.

As discussed earlier, identifying and characterizing regulated genes is critical to the understanding of many physiological and pathological processes. But, experimental strategies that address the problem of identifying regulated genes are limited. Currently, there are essentially two biochemical approaches that can be pursued. One approach, known as "subtraction libraries" takes advantage of the potential of RNA to form hybrids with complementary DNA strands in liquid hybridization protocols (Schraml et al 1993; Rosenberg et al. 1994; Sturzl and Roth 1990; Fargnoli et al 1990). Provided that MRNA is isolated before and after stimulation of a cell type of interest, those kinds of RNA that are not represented in both stages should be left over following the subtraction. This approach has been employed with various degrees of success. Another suitable approach is PCR based and termed "differential display" (Liang and Pardee 1992; Liang et al 1993) It uses subsets of random PCR primers to amplify unique messages. This approach too has been employed with various levels of success. A possible caveat for both approaches lies in the fact that they require amounts of mRNA from substantially pure populations of cells that permit biochemical handling and analysis.

Another approach, based on large scale DNA sequencing has recently been shown to give information on the relative abundance of genes expressed in a certain type of cell. Automation and large scale DNA sequence analysis is yielding enormous numbers of cDNA sequences, termed expressed sequence tags (EST), from certain tissue (Adams et al 1993; Venter 1993). Establishing an EST profile, while laborious and requiring resources that exceed the capacities of most laboratories, can yield information on many different types of genes and their levels of expression. Using this approach, profiles of many expressed genes can be obtained, for example from a healthy tissue and a corresponding diseased tissue. The rationale of the approach, however, is that genes which are differentially expressed are associated with the disease. Although this approach requires resources and sufficiently large quantities of tissue, it provides a feasible way to study gene expression. One of the major limitations of this method is that it favors genes expressed at higher levels.

Strategies that rely on integration of promoterless selectable marker genes to identify active chromosomal loci and to transcriptionally mark regulated genes were first described in bacteria (Casadaban and Cohen 1980). These authors used the lactose gene as a reporter gene to identify transcriptionally active endogenous promoters. Following the identification of the regulatory sequences, the genes could be isolated, sequenced and identified. In the eukaryotic cells the β-galactosidase reporter gene has been used to detect chromosomal activity in many cell lineages. This "trap" strategy has been applied to eukaryotic transcription units and cell specific enhancers, promoters and poly(A) sequences have been identified. Several enhancer trap vectors have been described that possibly allow the identification of enhancer sequences. A second kind of trap vector has been described in the mouse, the "gene trap". Gene trap vectors were designed to generate spliced fusion transcripts between the reporter gene and the endogenous gene present at the site of integration. (Gossler et al., 1989).

Regulation of gene expression, as measured by the activity of the active protein produced, occurs on many different levels. At the level of mRNA it includes, among others, transcription, RNA processing (splicing), RNA transport and/or MRNA stability (Mitchelson 1993; Elela et al 1992). At the level of protein synthesis it includes translation as well as post-translational modifications and processing (Richter, 1993)

While the basic principle of the enhancer/gene trap was established several years ago, its utility has been limited largely due to either the low efficiency in trapping loci or the lack of on/off selection for regulated loci. This basic fact is resembled in the modest body of literature published on studies related to promoter/enhancer/gene traps (Casadaban and Cohen 1980; Chu and Sharp 1981; Weber et al 1984; deGregori et al 1994; Hill and Wurst 1993; Niwa et al 1993; Chang et al 1993; Joyner et al 1992; Skarnes et al 1992; Joyner 1991; Reddy et al 1991,1992; Macleod 1991; von-Melchner 1990,1992; Gossler 1989; Friedrich and Soriano 1991; Soriano 1991)

In contrast, the present invention relates to a novel gene trap that allows for high efficiency identification and selection of regulated loci in eukaryotic cells using viral vectors into which the novel gene trap has been incorporated, cell into which the gene trap has integrated, methods for the identification of genes that are regulated at the level of MRNA, either transcriptionally or RNA stability, using the novel gene trap, and the recognition of its many and varied utilities.

In one aspect, the invention provides a gene trap construct suitable for in vitro and in vivo selection for regulated genes endogenous to a eukaryotic cell.

In one embodiment of this aspect, the nucleic acid construct comprises in downstream sequence (i) a cassette having a functional splice acceptor, a translational stop sequence and an internal ribosome entry site and (ii) a promoterless protein coding sequence encoding at least one polypeptide providing positive and negative selection traits. Preferably the functional splice acceptor is a splice acceptor consensus sequence. Also, preferably, the internal ribosome entry site can be a mammalian internal ribosome entry site, such as an immunoglobulin heavy chain binding protein internal ribosome binding site, or can be a picornavirus internal ribosome entry site, such as one derived from the encephalomyocarditis virus or the poliovirus. Also, the promoterless protein coding sequence can preferably encode a single polypeptide providing positive and negative selection traits. Alternatively, the promoterless protein coding sequence can encode a single protein whose expression and non-expression can be detected as positive selection traits, respectively. For example, the single protein cell encoded can be selected from the group consisting of hypoxanthine guanine phosphoribosyl transferase (HGPRT) and β-galactosyltransferase. Alternatively, the promoterless protein coding sequence can encode a fusion protein having first and second polynucleotide sequences whose expression can be detected as positive and negative selection traits, respectively. For example, the first polypeptide sequence can be selected from another group consisting of a functional neomycin phosphotransferase and a functional hygromycin phosphotransferase. The second polypeptide sequence can be, for example, thyrnidine kinase. Alternatively, the promoterless protein coding sequence can comprise operably linked first and second nucleic acid sequences encoding separate proteins respectively providing positive and negative selection traits and an internal ribosome entry site therebetween.

In another embodiment of this aspect, the promoterless protein coding sequence includes a translation stop sequence and further comprises a functional splice donor sequence downstream therefrom, but lacks a polyadenylation signal in cis downstream of the promoterless protein coding sequence. The above-preferred configurations and examples of the above embodiment are equally applicable to this embodiment.

Another aspect of the invention provides a viral vector incorporated with the nucleic acid constructs described above. Preferably the viral vector is derived from a retrovirus.

In one embodiment of this aspect, the retrovirus-derived vector comprises in downstream sequence (a) an integration sequence and (b) a nucleic acid construct comprising in downstream sequence (i) a cassette having a functional splice acceptor, a translation stop sequence and an internal ribosome entry site and (ii) a promoterless protein coding sequence encoding at least one polypeptide providing positive and negative selection traits. The preferred configurations and examples described above for the nucleic acid construct are likewise applicable in this vector.

In another embodiment if this aspect, the retrovirus-derived vector comprises in downstream sequence (a) an integration sequence and (b) a nucleic acid construct comprising in downstream sequence (i) a cassette having a functional splice acceptor, a translation stop sequence and an internal ribosome entry site and (ii) a promoterless protein coding sequence which comprises operably linked first and second nucleic acid sequences encoding separate proteins respectively providing positive and negative selection traits and an internal ribosome entry site therebetween. The preferred configuration and examples described above are likewise applicable here.

In another embodiment the retrovirus-derived vector comprises in downstream sequence (a) an integration sequence and (b) a nucleic acid construct comprising an downstream sequence (i) a cassette having a functional splice acceptor, a translation stop sequence and an internal ribosome entry site and (ii) a promoterless protein coding sequence that encodes at least one polypeptide providing positive and negative selection traits and includes a translation stop sequence, and (iii) a functional donor sequence which lacks a polyadenylation signal in cis. The above described preferred configurations and examples are likewise applicable in this embodiment.

In another aspect, the invention provides a eukaryotic cell into which the above vector has been integrated. Preferably the eukaryotic cell is a pluripotent cell, more particularly a stem cell such as an embryonic stem cell.

Another aspect of the invention provides a method for identification of genes whose activity is regulated upon a cellular transition event by introducing the viral vector described into a cell and observing expression of the positive and negative selection traits before and after the transition event.

In another embodiment, the invention provides a method for identification of genes whose activity is regulated upon a cellular transition event by introducing the viral vector described above as further containing a translation stop sequence and a functional splice donor sequence and which lacks a polyadenylation signal in cis and observing the stability of mRNA transcribed from such genes before and after the transition event.

FIG. 1 shows a schematic illustration or flow chart of the genetic selection protocol for regulated genes in accordance with the invention. An initial pool of cells is cultured to a population of about $5 \times 10^7$ to $5 \times 10^8$ cells per plate, which are then transduced/infected with the gene trap viral vector of the invention. Thereafter, selection for integration of virus in the genome of the cells that have been infected is performed with a hygromycin selection realizing about 107 cell clones (Hygro), with an efficiency of infection of about 10 to 50%. Thereafter, selection of active loci is performed on cells with the neomycin analog G418 to realize about $5 \times 10^5$ cell clones and selection for inactive loci is done with Gancyclovir to realize about $9.5 \times 10^6$ cell clones. The ratio of trapped active to inactive loci is about 1:0.05. Thereafter, conditions are switched to growth condition B, i.e., differentiated growth conditions. Counter-selection for loci that have switched from active to inactive due to cellular differentiation is accomplished with Gancyclovir and probably yields a relatively small number of independent cell clones (<100). Counter-selection for loci that have become activated in the differentiation process and are selected in G418 yield a number of independent clones that probably is in about the same order of magnitude. These are, respectively, in selections for genetic loci that are turned off upon differentiation and selection for genetic loci that are turned on upon differentiation. An efficiency of trapped regulated loci of about 10-4 is realized.

Figure 2:
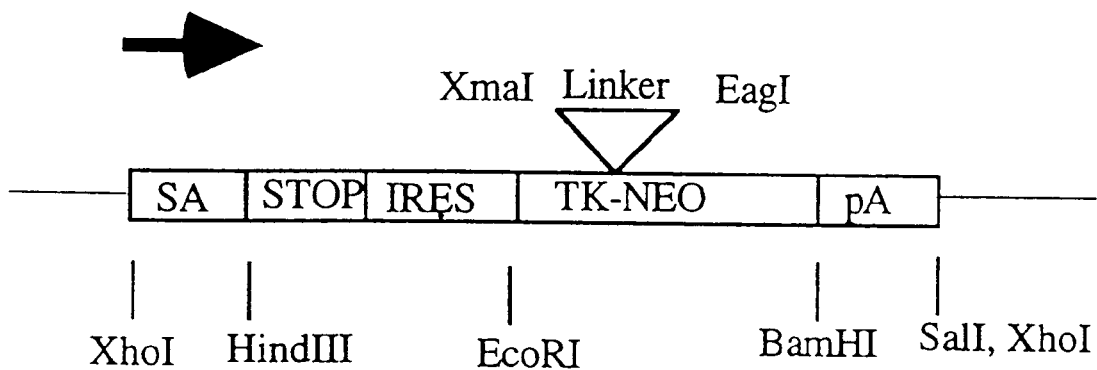

FIG. 2 shows a schematic diagram of one nucleic acid construct of the invention. The basic components of this positive/negative selection gene trap ("SATEO") are as follows. SA: adenovirus splicing acceptor; a stop sequence. IRES: internal ribosome entry site (e.g., BiP sequence); TK-NEO: thymidine kinase and neomycin phosphotransferase fusion gene. pA: PGK-1 poly adenylation signal. Arrow indicates the direction of transcription.

Figure 3:
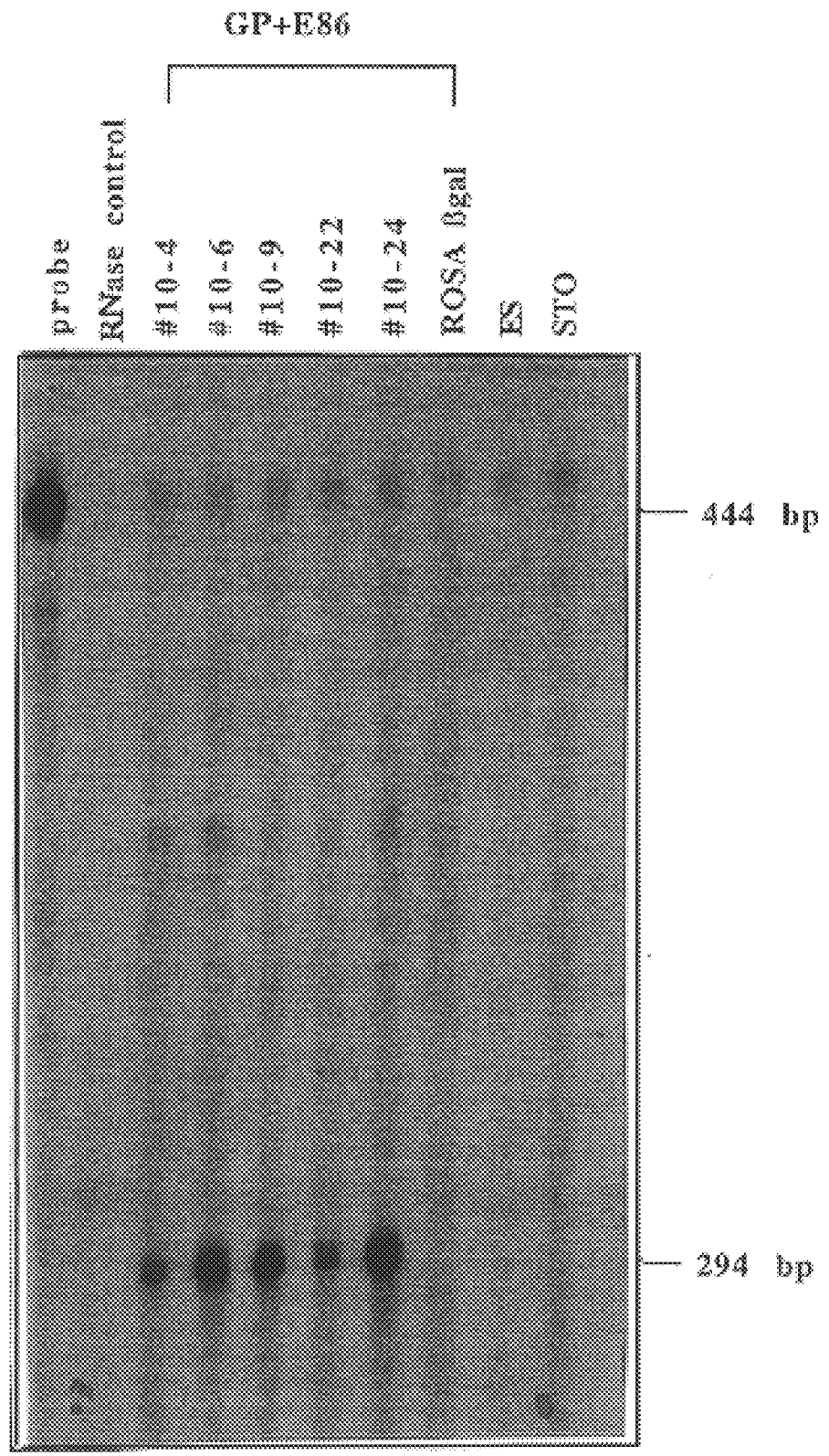

FIG. 3 is a photographic representation of an autoradiograph of a slab polyacrylamide gel used to size separate fragments of $^{32}$P-labeled RNA (Riboprobe, Promega) obtained from RNase protection analysis of gene trap transfected cells. Protection from degradation by RNAse A and RNAse T1 of a 294 bp fragment of a radiolabelled RNA probe is observed with RNA from 5 independent clones of cells transfected with the gene trap construction described in FIG. 2. This RNAse protection analysis provides evidence that the splice-acceptor consensus sequence within the trap is functional, linking the open-reading-frame (ORF) of the selectable markers to cellular messenger RNA which is as yet unidentified.

Figure 4:
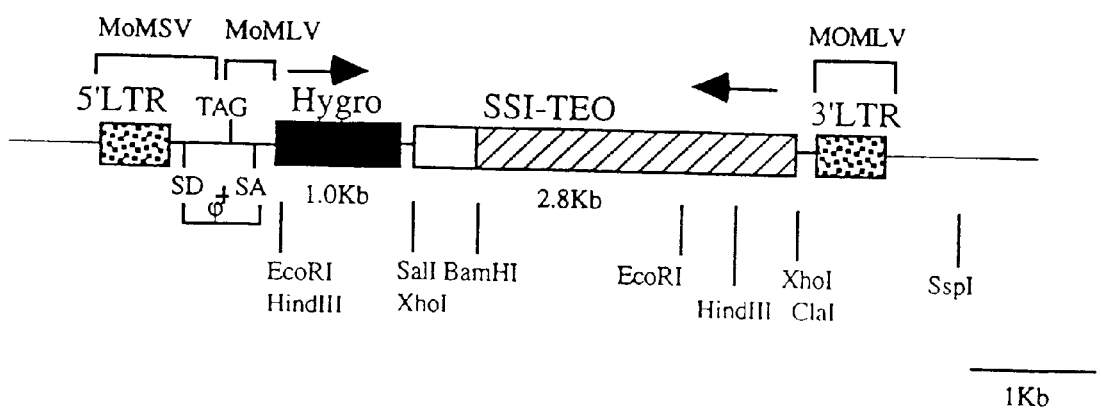

FIG. 4 is a schematic diagram of the elements of a gene trap retroviral vector in accordance with the invention. The plus/minus selection gene trap in pLNCX vector is shown. "Hygro" is hygromycin phosphotransferase; MoMSV: moloney murine sarcoma virus; MoMLV: Moloney murine leukemia virus; SATEO: SA-STOP-IRES- TK-NEO pA fusion gene. Blank bar represents PGK-1 poly A. Arrow indicates the direction of transcription.

Figure 5:
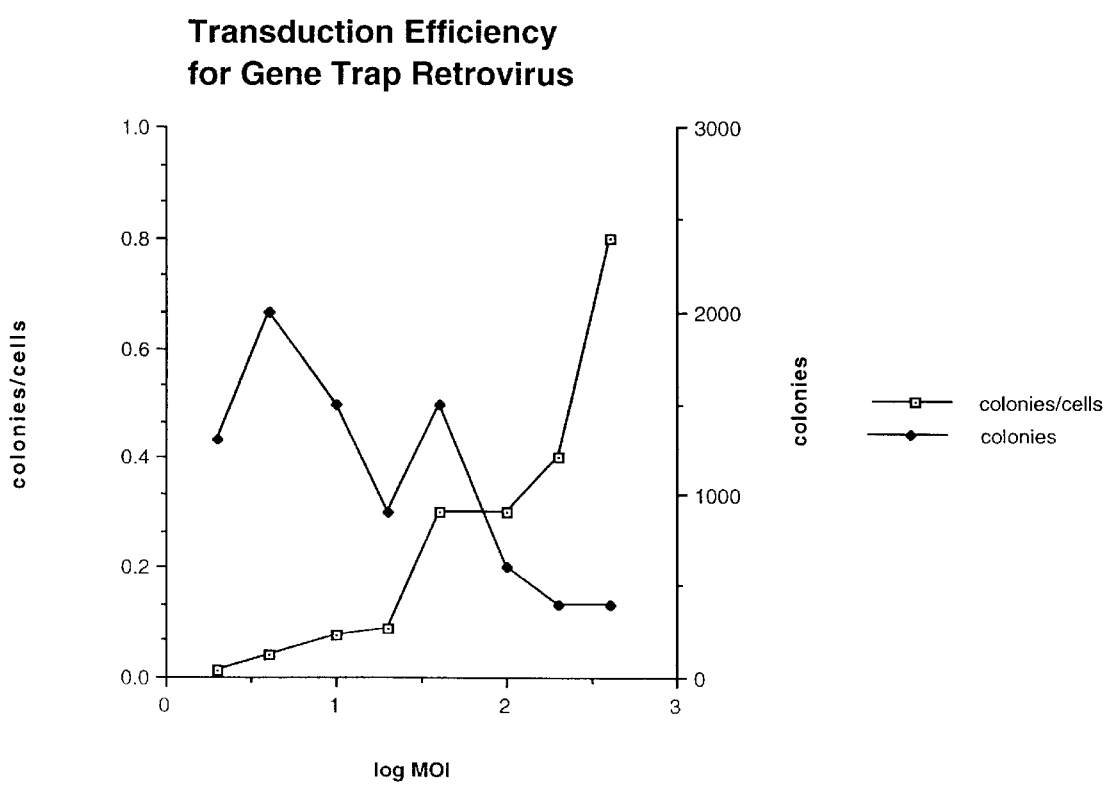

FIG. 5 is a graph showing the transduction efficiency of mouse embryonic stem cells using the gene trap retrovirus. The double graph shows the total number of colonies (closed squares) and the ratio of colonies/cells input (open squares) as a function of the multiplicity of infection of viral particles.

Figure 6A:
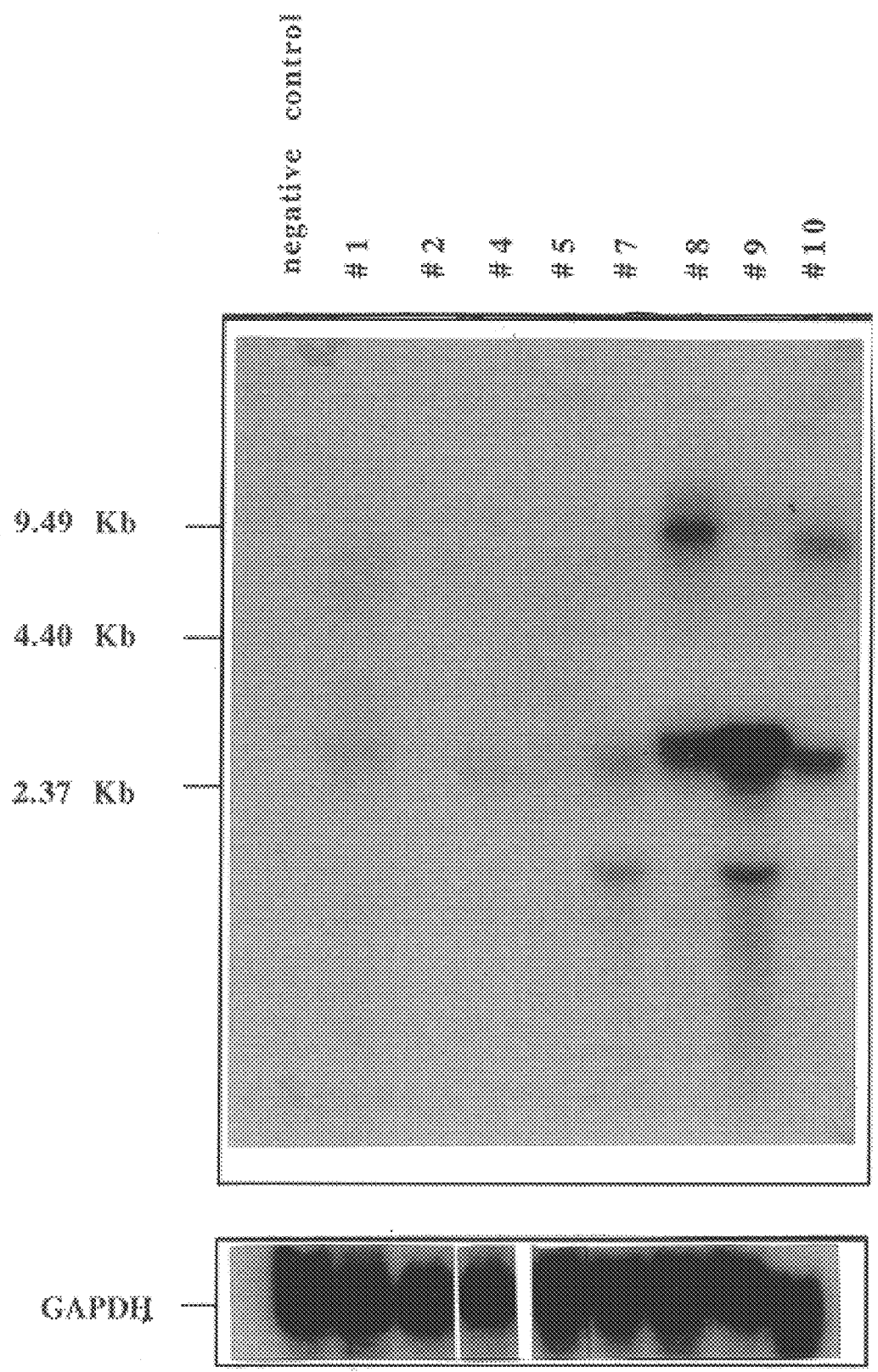

FIG. 6A is a photograph of an autoradiograph from Northern analysis. Specifically, an RNA blot on a Nylon membrane containing total cellular RNA purified from mouse embryonic stem cell-clones transduced with the gene trap retrovirus of the invention following positive selection, and probed with a $^{32}$P-labeled fragment of the neomycin gene. The bands indicate the various levels of neo-RNA generated form cellular promoters upon integration into active loci.

Figure 6B:
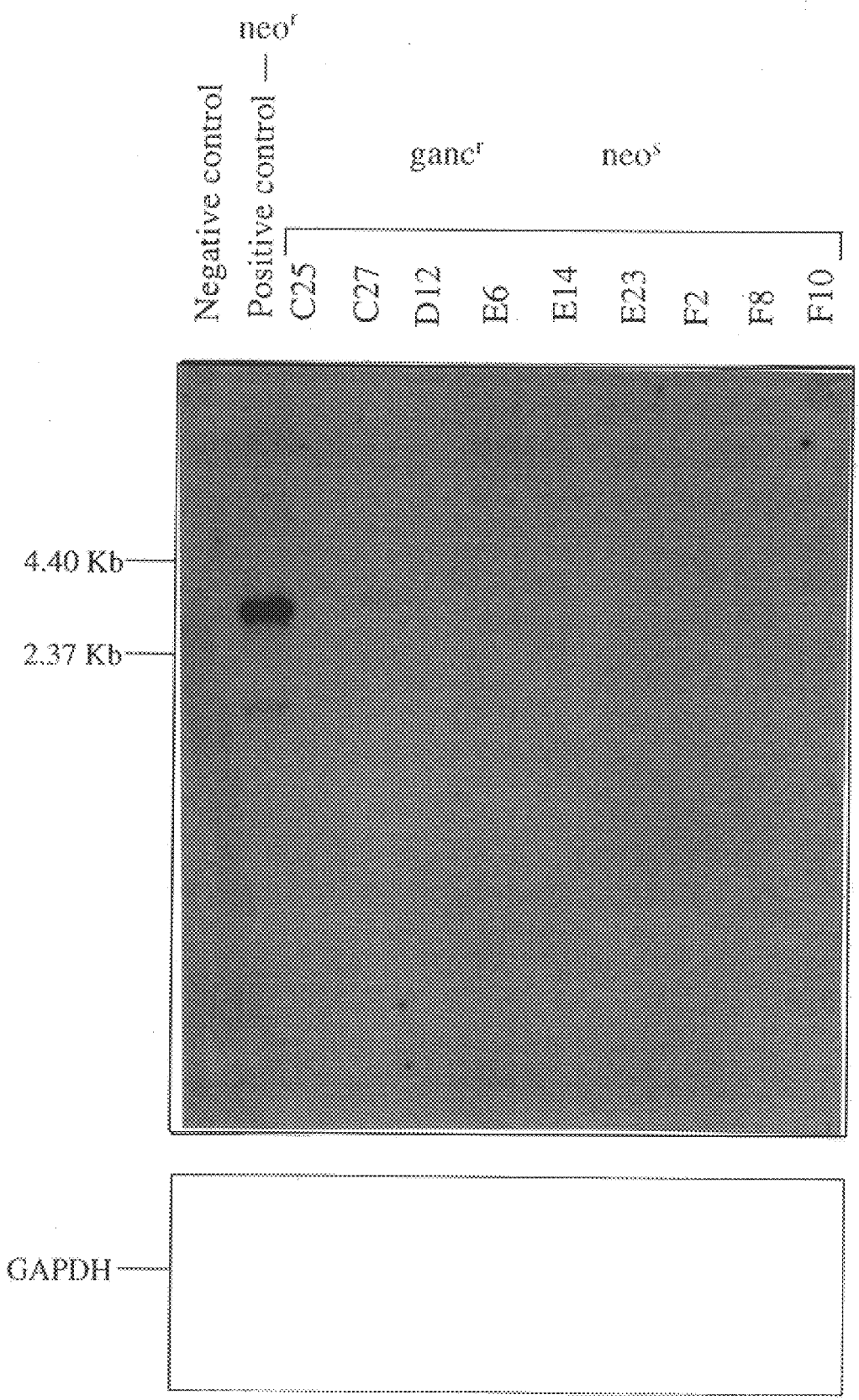

FIG. 6B is a photograph of an autoradiograph from Northern analysis of RNA isolated from clones of ES cells transduced with the retroviral vector of the invention, positive selection followed by differentiation and negative selection. The absence of bands in most lane indicates that cells that survived the negative selection process were no longer expressing the selectable marker genes of the trap from the cellular promoters.

Figure 7:
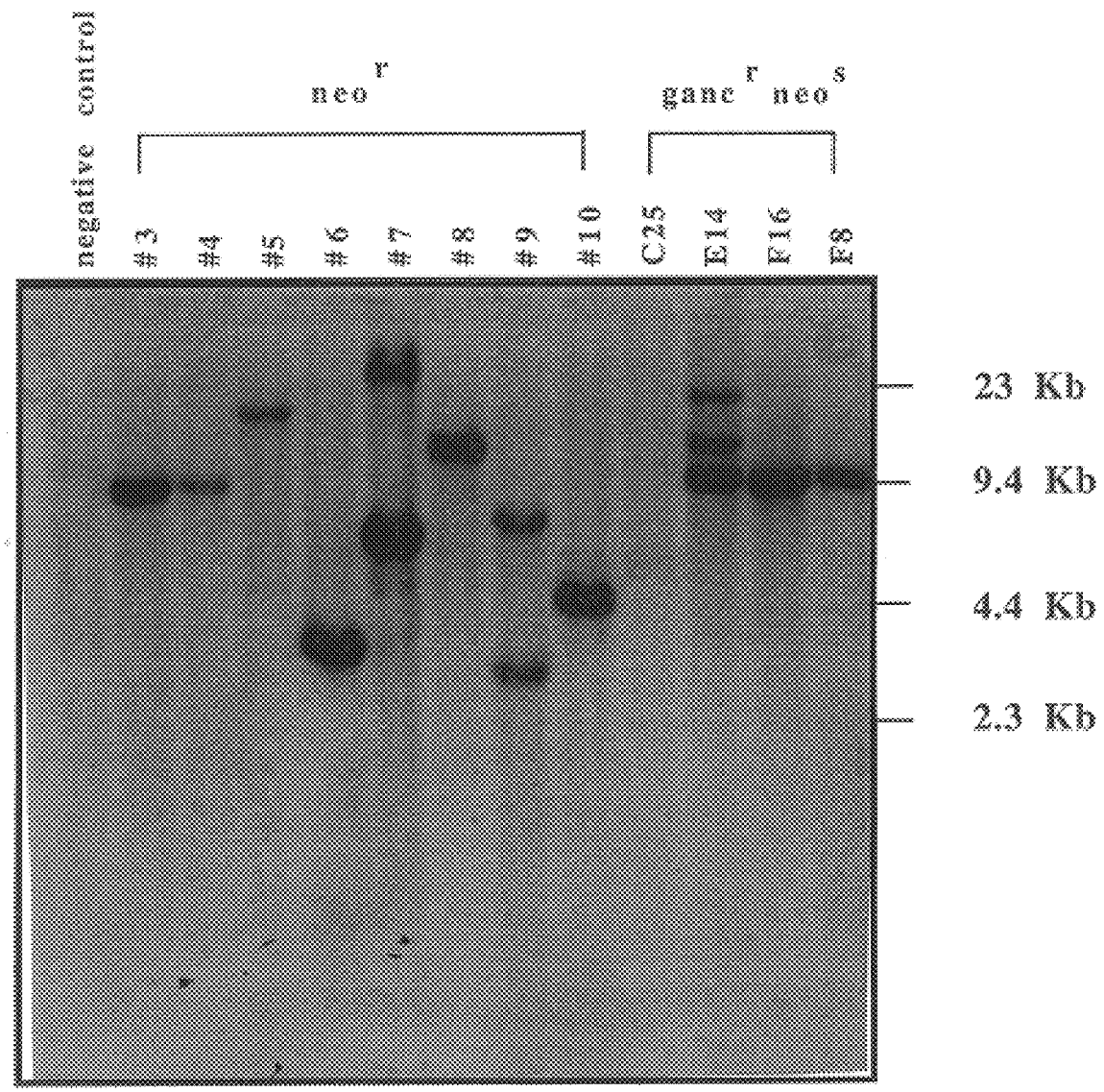

FIG. 7 is a photograph illustrating a Southern blot autoradiography of genomic DNA isolated from mouse embryonic stem cells transduced with the retroviral gene trap as described above, cut with BamHI and probed with a $^{32}$P-labeled fragment of the neomycin gene.

The term "promoterless" refers to a protein coding sequence contained in a vector, retrovirus, adenovirus, adeno-associated virus or retroviral provirus that is not under the control of a promoter within the vector, whether it be in RNA or DNA form. The vector, retrovirus or otherwise, may contain a promoter, but that promoter cannot be positioned or configured such that it regulates the expression of the promoterless protein coding sequence.

The term "protein coding sequence" means a nucleotide sequence encoding a polypeptide gene which can be used to distinguish cells expressing the polypeptide gene from those not expressing the polypeptide gene. Protein coding sequences include those commonly referred to as selectable markers. Examples of protein coding sequences include those coding a cell surface antigen and those encoding enzymes. A representative list of protein coding sequences include thymidine kinase, .-galactosidase, tryptophane synthetase, neomyocin phosphotransferase, histidinol dehydrogenase, luciferase, chloramphenicol acetyltransferase, dihydrofolate reductase (DHFR); hypoxanthine guanine phosphoribosyl transferase (HGPRT), CD4, CD8 and hygromycin phosphotransferase (HYGRO).

The term "functional splice acceptor" refers to any individual functional splice acceptor or functional splice acceptor consensus sequence that permits the vector of the invention to be processed such that it is included in any mature, biologically active mRNA, provided that it is integrated in an active chromosomal locus and transcribed as a contiguous part of the premessenger RNA of the chromosomal locus.

The term "translational stop sequence" refers to a sequence that codes for the translational stop codons in three different reading frames. This translational stop sequence is physically located downstream (3') of the splice acceptor sequence, but upstream (5') of the selectable marker fusion protein translation initiation site. It causes truncation of the peptide chain encoded by exons upstream of the retroviral vector at the chromosomal locus. It also prevents the translational reading frame of the genomic locus from proceeding into the selectable marker gene of the invention, thus preventing potential translation of it in a non-sense reading frame.

The term "internal ribosome entry site" (IRES) is an element which permits attachment of a downstream coding region or open reading frame with a cytoplasmic polysomal ribosome for purposes of initiating translation thereof in the absence of any internal promoters. An IRES is included to initiate translation of selectable marker protein coding sequences. Examples of suitable IRESes that can be used include the mammalian IRES of the immunoglobulin heavy-chain-binding protein (BiP). Other suitable IRESes are those from the picornaviruses. For example, such IRESes include those from encephalomyocarditis virus (preferably nucleotide numbers 163–746), poliovirus (preferably nucleotide numbers 28–640) and foot and mouth disease virus (preferably nucleotide numbers 369–804). Thus, the viruses are located in the long 5' untranslated regions of the picornaviruses which can be removed from their viral setting in length to unrelated genes to produce polycistronic mRNAs.

The term "operably linked" refers to an arrangement in which evidence of biological activity from one marker implies the biological activity from a second marker is also present in the same cell. Operably linked can also mean that both the positive and negative selectable marker genes are encoded by the same transcription unit. Translation of both such markers can be regulated by various modes, including cap-dependent translation of the open-reading-frame (ORF) located furthermost 5' on the transcription unit. Translation of the ORF located downstream of the first ORF can be regulated by an IRES. Alternatively, both selectable marker genes can be encoded by one ORF, yielding one contiguous polypeptide with both biological activities. The term operably linked is also used to refer to nucleotide sequences which are linked in the proper reading frame, whether to encode an MRNA transcript of a desired gene product or for a desired regulatory control.

The term "assaying for the expression" of a protein coding sequence means any test or series of tests that permits cells expressing the protein to be distinguished from those that do not express the protein. Such tests include biochemical and biological tests and use either "selectable markers" or "assay markers."

The term "detectable marker" encompasses both the selectable markers and assay markers. The term "selectable markers" refers to a variety of gene products to which cells transformed with a retroviral construct can be selected or screened, including drug-resistance markers, antigenic markers useful in fluorescence-activated cell sorting, adherence markers such as receptors for adherence ligands allowing selective adherence, and the like.

The term "assay markers" refers to a variety of gene products that can be detected in experimental assay protocols, such as marker enzymes, antigens, amino acid sequence markers, cellular phenotypic markers, nucleic acid sequence markers, and the like.

The terms "recombinant virus vector" refers to any recombinant ribonucleic acid molecule having a nucleotide sequence homologous or complementary with a nucleotide sequence in an RNA virus that replicates through a DNA intermediate, has a virion RNA and utilizes reverse transcriptase for propagation of virus in a host cell. Such viruses can include those that require the presence of other viruses, such as helper viruses, to be passaged. Thus, retroviral vectors or retroviruses are intended to include those containing substantial deletions or mutations in their RNA.

The term "control region" refers to that region of the recombinant virus or viral vector that is duplicated after infection and prior to integration. Control regions of the retrovirus include U3 and U5 regions. Such regions also include long terminal repeat (LTR) regions.

The term "host cell" encompasses mammalian and other cells that can be transfected or transduced by the subject retroviral vector construct. The term as used herein means any eukaryotic cell which may be in culture or in vivo as part of a unicellular organism, part of a multicellular organism, or a fused or engineered cell culture. The cell also may be part of an animal, and in one aspect of the invention, is part of a transgenic animal.

The term "integration sequence" refers to any nucleic acid sequence which, when contacted with genomic DNA under appropriate conditions, causes the nucleic acid sequence or a portion thereof to fuse with the genomic DNA of the host cell. Such integration sequences when used to introduce a protein coding sequence into the genomic DNA result in a fusion involving no damage to the protein sequence and conservation of a portion of the integration sequence. Such integration sequences cause minimal damage to genomic DNA, except for interrupting the genomic sequence. Integration sequences include those known to occur in the control regions which are responsible for the integration of the retrovirus into genomic DNA. Such integration sequences may be included in circularized nucleic acids or in linear nucleic acids.

The term "polymerase chain reaction" or "PCR" refers to a procedure described in U.S. Pat. No. 4,683,195, the disclosure of which is incorporated herein by reference.

The term "primer" refers to a nucleic acid which, when hybridized to a strand of DNA, is capable of initiating the synthesis of an extension product in the presence of a suitable polymerization agent. The primer preferably is sufficiently long to hybridize uniquely to a specific region of the DNA strand.

Any ectopically overexpressed molecule that can be screened in a defined assay system qualifies as a positive or negative selectable marker gene. Selectable markers include any gene that can cause a dominant mutation, i.e., mutations that cause gain of function and display a phenotype if the mutant genotype is present only in one allele. The presence or absence, the positive or negative selection, of such a dominant effect is one that is readily detectable, and the cells are those that can be sorted based upon the expression of such a dominant effect. A single gene or multiple genes can be used for positive or negative selection. Positive selection refers to the isolation of cells that express the marker gene, whereas negative selection refers to the isolation of cells that do not express the marker gene.

The insert causing dominant phenotypes can include drug resistance genes. Examples of such drug resistance genes include the neomycin phosphotransferase, hygromycin phosphotransferase and puromycin phosphotransferase genes. Expression of such positive selectable marker genes is made detectable by supplementing the culture medium with the corresponding drug, G418, hygromycin and puromycin, respectively. Further positive selectable markers include but are not limited to histidinol-dehydrogenase, chloramphenicol-acetyl transferase(CAT), dihydrofolate reductase (DHFR), hypoxanthine guanine phosphoribosyl transferase (HPRT) for selection of HPRT- cells in medium supplemented with hypoxanthine, aminopterine and thymidine (HAT).

Negative selectable marker genes can be included in expression cassettes. Such genes include the herpes simplex virus-thymidine kinase (HSV-TK) genes, as well as genes encoding various toxins including the diphtheria toxin, the tetanus toxin, the cholera toxin and the pertussis toxin. A further negative selection marker gene is the hypoxanthine-guanine phosphoribosyl transferase (HPRT) gene for negative selection in 6-thioguanine.

The expression of positive/negative reporter or selectable marker genes can be detected, using a fluorescent activated cell sorter (FACS) for observing emission of light of a specific wave length. For example, a protein that spontaneously emits light and can serve as reporter as well as a positive/negative selectable marker in FACS analysis, is the Green Fluorescent Protein (GFP) isolated from the bioluminscent jellyfish Aequorea victoria. FACS analysis and FACS sorting make it possible to isolate cells that emit light as well as those that do not. For example, the reporter or selectable marker gene can include the bacterial β-galactosyltransferase which could be used in combination with a vital stain consisting of a fluorescent dye whose emission spectrum could depend on cleavage of a β-glycosidic structure. Subsequent to staining of live cells with the substrate for β-galactosidase, FACS analysis would be employed preferentially to isolate either expressing or non-expressing cells.

Selectable markers include genes that allow for identification, selection and/or sorting of cells based upon cell surface expression of proteins that normally would not be expressed and would not interfere or adversely affect the biological properties of the cells. Suitable selectable marker genes include cell-cell adhesion molecules including ICAMs, cadherins or selections that normally are not expressed on the cell of interest, and which do not cross-react with endogenous ligands. Expression of such markers can be detected using specific antibodies, or other forms of natural ligands, in combination with sorting protocols including panning or FACS. In one example, the marker includes a truncated form of a heterologous IL-3 receptor (swine form in mouse cells, human form in swine cells) that is incapable of transducing a signal into the cell. Expression of this receptor is then monitored using the natural ligand (swine or human IL-3) which is preferably conjugated with a fluorescent dye or an enzyme that detectably converts a chromogenic substrate.

Positive/negative selection is preferably achieved using cell-substrate adhesion molecules including integrins that normally are not expressed by the biological system, i.e., in the cell types of interest such as the mouse embryonic stem cells, miniature swine embryonic stem cells as well as mouse, porcine and human hematopoietic stem cells.

Other molecules useful as dominant selectable genes include glycosyltransferases of a defined specificity that can be assayed. Other positive selectable marker genes include cell surface molecules expressed on cells that normally do not express that gene. Such molecules include cell-cell adhesion molecules (CAM), such as the selecting. They also include cell-substrate adhesion molecules such as the integrins and cadherins. Other positive selectable markers includes enzymes involved in post-translational processing of polypeptides that confer dominant effects, like attachment of oligosaccharide chains by glycosyltransferases.

Negative selectable marker genes are genes that when expressed lead to selective elimination or death of their host cells. One example of the negative selectable marker of the invention is the herpes simplex virus (HSV)-thymidine kinase (TK) gene for selective killing of cells expressing TK in the presence of any of the nucleoside analogs acyclovir, gancyclovir or 5-Fluoro-Iodo-Amino-Uracil (FIAU). Other suitable negative selectable marker genes include genes that cause selective death, blocking of cell adhesion or expose cell clones to growth disadvantages. Such negative selectable markers include diphtheria toxin (DTX), pertussis toxin, cholera toxin or activators of apoptosis (programmed cell death), such as the bc12-binding protein (BAX).

Positive and negative selection can also be achieved with a single drug selectable marker gene that encodes an enzyme for a nucleotide synthesis salvage pathway. One suitable gene of this class of enzymes is the hypoxanthine-guanine phosphoribosyltransferase (HPRT) gene which is used for positive selection in medium supplemented with hypoxanthine, aminopterin and thymidine (HAT). Negative selection is preferentially achieved by selection in a nucleoside analog including 6-thioguanine (6TG). HPRT is a cellular gene, on the X chromosome, whose function is not essential for growth and survival of cells in vitro. It appears, however, that its function is necessary for proper biological function of certain nerve cells in vivo.

Expression of the positive and negative selection traits within one polypeptide chain allows for the flexibility of either positive or negative selection of cells expressing the single fusion protein. The invention can also include a combination of positive and negative selectable marker genes expressed on one transcription unit and translated as two independent polypeptides. Translation of the second polypeptide is regulated by an internal ribosome binding site (IRES) located in cis and operably linked to the second protein coding region.

The gene construct encoding the HSV-TKneo fusion protein lacks operably linked endogenous regulatory elements in cis that would confer endogenous transcriptional activity. Instead, according to the invention, located in cis are DNA sequences that functionally regulate mechanisms like mRNA processing, including splicing.

An IRES is included to initiate translation of the TK-neo fusion protein, which is the second cistron and is located downstream from the first ATG of a contiguous strand of mature MRNA. The IRES is positioned downstream, 3' of the translational stop sequence and upstream of the protein coding region of the TK-neo fusion protein. Host cells expressing the TK-neo fusion gene upon its integration at any random active chromosomal locus become sensitive to positive selection in the presence of G418, as well as negative selection in presence of acyclovir, gancyclovir or FIAU.

In a preferred embodiment genetic elements that are essential to the identity of a eukaryotic exon include functional splice-acceptor consensus sequences. The splice acceptor preferably links the pre-mRNA from genes encoding the dominant reporter to the upstream splice donor from an active chromosomal locus and is essential for the reporter gene to be included in the mature processed mRNA. Such a splice acceptor sequence may include around 100 nucleotides of the 5' splice junction of the adenovirus. The splice acceptor used is included ubiquitously in all splicing reactions, such that it is included in most, if not all, processed mature messenger RNA molecules.

Splice acceptor sequences can also be derived from exons of cellular genes that are expressed constitutively as well as ubiquitously including β-actin, PGK-1, HPRT. Preferably, splice acceptor sequences are not derived from a region of DNA that includes the 5'-splice junction of exons which are subject to alternative splicing, either tissue specifically, cell-type specifically or stage specifically.

Intron/exon junctions do not correspond or follow a particular rule related to the conservation of the open reading frame (ORF), i.e., junctions (intron-exon breakpoints) may be at any position within a codon. Provided that any one position of a codon can include the intron/exon junction, gene trap reporters whose ORF starts at that junction would be translated in the proper frame at an approximate probability of 1/3 only. Therefore, to increase the probability for translation of the reporter to occur in the proper frame, an IRES has been included to initiate translation of an internal ORF within a polycistronic message. Translation initiation within a polycistronic RNA using an IRES is thus independent of the reading frame of the preceding cistron. Also, the IRES includes a functional sequence that can initiate translation of a messenger RNA that lacks a 5-methylcap modification. As noted above, in a preferred embodiment of the invention, an IRES can be derived from the immunoglobulin binding protein, GRP79, also termed BiP. The IRES can also be derived from a picornovirus, such as the encephalomyocarditis virus (EMCV) or poliovirus.

Both the splice acceptor consensus sequence and the IRES sequence are separated by a series of stop codons in all reading frames to ensure that translation of the preceding ORF is terminated/truncated upstream of the IRES that causes new-initiation of translation. All these elements are sequentially organized as described above on one linear DNA molecule and are located upstream (5') of and operably linked to the genes encoding the dominant selectable markers. These elements are enabling, but not causal to the expression of the dominant reporter genes.

The nucleic acid construct of the invention can be incorporated into a viral vector, such as a retrovirus, adenovirus or adeno-associated virus vector, for efficient delivery to eukaryotic cells. The resultant recombinant vector can transduce dividing cells, and upon infection, can integrate its genome at random sites in chromosomal DNA of host cells. In one embodiment, the retroviral vector carries a mutation in the transcriptional enhancer of the U3 portion of the 3' LTR. Based upon the rules that govern retroviral transcription from a provirus (DNA-form of the virus when integrated into host chromosomes) to produce viral RNA (viral genome to be packaged or translated to generate viral proteins or recombinant gene products), the provirus carrying the mutation in the U3 region should be transcriptionally inactive. A suitable vector containing this property could include the pGen- vector, derived from MoMLV. In situations where interference of transcriptional activities between the viral LTR and the chromosomal loci might be a concern, the pGen- vector could have advantageous properties. In a preferred embodiment, the trap vector is included in the LNCX retroviral vector including the MOMLV 5' LTR and Moloney Murine Sarcoma Virus (MoMLV) 3' LTR.

A retroviral vector will have LTRs derived from one or several types of retroviruses, and the LTRs may be genetically modified to achieve desired properties in the cell type of interest such as in embryonic stem cell derived from mouse, pig or human, or a hematopoietic stem cell derived from various mammalian origins. One suitable vector displaying such properties is the retroviral vector PLNX (Miller and Rosman 1989) or derivatives thereof. The retroviral vector can also include regulatory elements suitable for propagation and selection in E. coli which include an origin of replication (ori) and an antibiotic resistance marker for selection ($Amp^R$).

Alternatively, delivery of the molecular tag or gene trap to the host cell to monitor gene activity can be achieved using electroporation. Electroporation is a feasible approach for delivery of the gene trap to certain types of cells including embryonic stem cells or hematopoietic stem cells. Generally, the efficiency of generating stable transformants of eukaryotic cells is somewhat lower than with retroviral vectors, but is preferable in cases where the cells are refractory to viral infection or integration of the provirus into the host chromosome.

Delivery of the vector into host cells can also be achieved by liposome-mediated transfection, calcium phosphate precipitation as well as DAE-dextran or other techniques well known to those in the field. See Sambrook and Maniatis (1989). Lipofection can also be used so that the gene trap vector will become translocated across the plasma and nuclear membrane for stable integration into random sites of the chromosomes from cell types that are permissive for lipofection, including mouse embryonic stem cells.

The vector can be introduced to ecotropic producer cell lines to yield virus that infects mouse cells only. Furthermore, the viral trap vector can be packaged in amphotropic producer cell lines including AM 12 or PA317 (Miller and Rosman, 1989) to yield virus that can infect human or porcine cells, for example.

The vector is designed to deliver to cells a molecular tag (or trap) which includes one or several drug selectable markers. Upon integration of the molecular tag into chromosomal DNA, the activity of the endogenous gene at the locus of integration can be monitored using drug selection and, upon stimulation of the cells, genetic loci whose activity-shifts result in altered levels of steady state MRNA, can be molecularly identified and the corresponding genes isolated and characterized.

Regulation of gene expression as measured by the activity of the protein product can occur on many levels. At the MRNA level it includes transcription, RNA processing (splicing), RNA transport and/or mRNA stability. At the protein or protein synthesis level it includes translation, post-translational modifications and processing.

The general protocol for use of the gene trap vector of the invention is illustrated in FIG. 1. As shown, any gene regulated at the transcription and/or niRNA stability level is a suitable candidate for identification and isolation of regulated loci using the vector and the protocol of the invention. The disclosed protocol can be applied to any cell-type of interest that can be maintained in culture, at least transiently, and can be subjected to drug selection. Details for the protocol relate to the type of reporter/drug selectable marker gene employed in the gene trap. Use of a drug selectable marker such as Neo requires that the cells be cultured for a prolonged period of time, during which the cells can be subjected to selection by the corresponding drug. Alternative reporter genes including ectopically expressed cell surface markers or the green fluorescent protein can be assayed either by FACS analysis and sorting or by panning to particular substrates (Reddy et al., 1992)

The vectors and methods of the present invention have a broad array of utilities, including those discussed below.

Identifying Genes Regulated During Embryogenesis

Biological processes including development of multicellular organisms and differentiation of primitive embryonic cells into specialized tissues and organs are orchestrated by large sets of regulated genes that are organized in regulatory networks. Previously, mammalian species have, for the most part, not been accessible to molecular genetic analysis of developmental processes.

An exception is mouse strain 129/SV (Robertson, 1986), that became suitable for specific mutational analysis due to the recently developed targeted "gene knockout," or targeted gene replacement, technique used in embryonic stem cells. Except for the gene knockout approach, mammalian gene networks have not been identified by studying mechanisms of organogenesis and tissue differentiation in vitro. Further, data from such studies supported the notion that regulatory genes are interacting in an orderly fashion. In fact, the order within gene networks is established as a defined hierarchical cascade with master regulatory genes as triggers.

A family of master regulatory genes was identified and is being characterized in the cellular lineage of skeletal muscle differentiation. It consists of several members of DNA binding proteins termed MyoD (Thayer et al. 1989). Molecular analysis of muscle differentiation became feasible because of the availability of a tissue culture system that could reliably be induced to differentiate in vitro into skeletal muscle. The cell line 1OT 1/2 can differentiate along various lineages and normally fits the characteristic of a fibroblast. However, when exposed to certain culture conditions, it differentiates into skeletal muscle or adipocytes. Induction of differentiation is achieved upon culture of these cells in 5-azacytidine. The replicating DNA becomes hypomethylated which may affect the pattern of gene expression. One gene, the cell line 1OT1/2, that apparently is affected in its level of expression by hypomethylation is the MyoD master regulatory gene, which causes muscle differentiation.

Most other tissue culture systems, including mouse embryonic stem cells, hematopoietic stem cells, as well as precursor and progenitor cells from many different tissues are suitable systems for identifying regulated genes. However, for the target reagents to be available at quantities that allow for biochemical analysis, the culture system should be homogeneous with regard to the initial cell population and also with regard to its fate under certain culture conditions, i.e., the type of differentiated cell should be homogeneous. The present invention provides a genetic tool to identify regulated genes on a clonal basis.

One cell type to be investigated includes the totipotent mouse embryonic stem cell that resembles the primitive ectoderm of the embryo proper. Primitive ectoderm can differentiate into all three germ layers of the embryo, i.e., ectoderm, mesoderm and endoderm. Subsequent to differentiation into germ layers, progeny of the ES cell can acquire the property of further specialized tissues including terminally differentiated cell types such as neurons, or cells of hematopoietic lineages. An important observation would be to identify those genes that confer identity to the ES cell phenotype. In using the present invention, the selection protocol would be designed to allow for selection of cell clones in which the gene trap is integrated in a locus that becomes turned off as the ES cells lose totipotency. Alternatively, genes that become up-regulated or transcriptionally active upon cellular differentiation may be critical for any or all of the differentiated cellular lineage. Theoretically, it should be possible to achieve saturation analysis of ES cell specific genes, to establish a type of "fingerprint" of genes expressed in the ES cell-type specific pattern. Identification of whole sets of cell-type specific genes then makes it possible to establish what genes are part of a cascade within a genetic regulatory network. Ultimately it should be possible to identify the master regulator genes that are essential in conferring ES cell identity. Understanding the regulation of these master regulatory genes would then yield information as to the genetic control of the primitive ectoderm lineage.

Identifying Genes Regulated During Tissue Differentiation

Alternatively, questions that can be addressed using the gene trap of the invention concern genes that become turned on as stem cells differentiate in culture, for example, preferentially along the hematopoietic lineage in the presence of all-trans retinoic acid, in the absence of Leukemia Inhibitory Factor/Differentiation Inhibiting Activity (LIF/DIA). Again the starting material is a batch of ES cells grown under conditions that maintain these cells undifferentiated. Selection conditions applied to these undifferentiated cells allow for survival of cells which have the trap integrated into an inactive locus (selection in Gancyclovir/FIAU). Cells expressing the trap selectable markers are selected against and die. After this initial round of selection, the surviving cells are grown up to a larger batch under conditions that allow the ES cells to differentiate. Then, selection conditions are reversed such that cells that are now expressing the trap will survive under drug selection conditions. Those clones of cells that survive both rounds of selection have the trap integrated in genetic loci that become upregulated or turned on upon stimulation. Provided that the induction of cellular differentiation is controlled (i.e., differentiation towards the hematopoietic lineage, the neuroectodermal lineage or the myogenic lineage) the regulated genes that were identified could be specific for differentiation into one or several of those lineages.

Identifying Oncogenes

Oncogenes are genes whose pattern of expression is associated with tumors, based on their ability to cause transformation of cells (Bishop 1983) . More specifically, these are dormant oncogenes since the overexpression of one allele in either the wildtype or a mutant form can cause loss of growth control of the affected cell. Another class of genes associated with tumors are those whose absence leads to loss of growth control and transformation. They are termed recessive oncogenes or tumor suppresser genes. Conceptually, it has been rather straightforward to identify oncogenes, either by a combination of genetic and biochemical approaches looking for dominant effects, namely for cells that lose growth control upon transfection with clones cDNAs isolated from tumor cells. Recessive oncogenes, however, have been cloned for the most part by positional cloning.

Identifying Genes Associated With Tumorigenesis

Primary tissue culture cells derived from human tissue, as well as tissues from other species are transduced with the gene trap vector and subjected to drug selection for survival of cells expressing or non-expressing the gene trap selectable marker genes. Following initial selection, the cells are subjected to treatment with a mutagen, e.g. EMS or UV radiation, and then cultured in soft agar for screening of foci formation. Alternatively, mutagenized cells are grown in immuno-compromised mice such as SCID or nu/nu for the generation of tumors. Tissues containing the transformed cells are then recovered and cultured. The tumor cells in culture are then subjected to drug selection, which now is directed to the opposite type of selection than the initial selection. Cells that survive the counter-selection are clonally grown, and subjected to molecular analysis for chromosomal loci of trap integration.

Identifying Genes Regulated Upon Tumor Formation

One unique property of cultured ES cells, as well as of primordial germ cells, is the formation of teratocarcinoma tumors when introduced into privileged sites (testes, kidney capsule) of an adult syngeneic or immunocompromised animal. A preferred embodiment of the invention includes the use of a gene trap suitable to select for chromosomal loci that are active or inactive, initially in ES cells and then also following transformation of the cells into teratocarcinoma tumors. In order to accomplish the genetic selection of such genes, a large batch of undifferentiated ES cells, grown in the presence of LIF are being transduced with retrovirus including the recombinant gene trap. From an initial batch of ES cell culture of around $10^7$ cells, approximately 10%, or $10^6$ cells have the trap integrated into an active locus and survive positive selection in G418. 90% of the cells will not express the trap and thus, will live if subjected to negative selection in gancyclovir. All cells of the either positive or negative selected groups are being kept separate and injected into the testis of SCID mice. Three to five weeks following injection of cells, enlargements of the scrotum become apparent. Depending on the size of those enlargements, the animals are sacrificed and the tumor tissues dissociated in a mild solution of trypsin and plated in culture dishes. Counter-selection for shift in activity of any regulated locus that has been trapped is performed on the cells derived from the teratocarcinomas. Those cells that survive counter-selection are grown clonally to obtain sufficient DNA for molecular analysis. Using DNA probes specific for the selectable marker genes in the trap, genetic clones are being isolated that analysis of genes at the locus of integration are then being, identified by using sequences from the chromosomal loci in Northern analysis comparing RNA from undifferentiated ES cells with RNA from cells derived from the teratocarcinomas. Analogous to other biological systems where the retrovirus gene trap was used to identify novel regulated genes, the function of those gene is being assessed using in vitro and in vivo transgenic approaches combined with gene knockout, site directed mutagenesis and dominant negative approaches.

Identifying Genes Related to T-cell Tolerance

A complex problem in immunology concerns the mechanisms of T cell tolerance, particularly the mechanisms that render T cells unresponsive rather than leading to clonal depletion or death of those cells that would normally react to a particular antigen, such as an allograft or xenograft. Either primary human T cells or T cell lymphoma cell lines that can respond in a mixed lymphocyte reaction (MLR) to allograft or xenograft stimulator cells are transduced with the gene trap retrovirus, divided into two different batches of at least $10^7$ cells, stimulated and subjected to either positive or negative selection. Cells that respond by proliferating upon stimulation and survive under conditions of drug selection, have the trap integrated at an active or inactive locus, respectively. Following the primary MLR combined with the drug selection, responder cells are exposed to conditions that normally induce tolerance. Subsequent to this tolerization, responder T cells again are exposed to drug selection, but in reverse mode. Cells that were initially subjected to positive selection, i.e. for expression of the trap are then exposed to specific drugs for negative selection. Clones of cells that survived both selections and were tolerized are subjected to further analysis including molecular cloning of the locus of integration of the gene trap. Genes encoded by the chromosomal locus of trap integration can then be identified, molecularly analyzed using Southern, Northern and RNase protection assays. When analysis reveals a correlation of the activity of any such locus with tolerance induction, it provides a method to determine the functional relevance of those genes. Overexpression of those genes in clonal T cells as well as somatic knockout experiments will reveal the potential implication of those genes in tolerance induction. Further in vivo analysis using transgenic animals to overexpress those genes, as well as gene knockout strategies will yield information as to whether any particular genes functions in a dominant or recessive fashion.

Diagnostic Reagents/Products For Monitoring Gene Activity

This can take the form of in vitro diagnostic approaches, including mutagenesis assays and also more subtle effects that simply affect the metabolic state of a cell.

Cell types that cause particularly devastating forms of tumors include some of the neural crest derived cells including the small cells of the lung, melanocytes, chromaffin cells in the adrenal medulla and parafollicular cells in the thyroid. Other cell types with a relatively high propensity for tumorigenic transformation include mammary epithelial cells and astroglias, for example. Such cells can be cultured to a population of around 107 to 108 cells to screen for chemical or other environmental parameters with mutagenic effects using the vector and method of the invention. The cells are transduced with the recombinant gene trap and subjected to the first round of selection. Taking into consideration that the transduction efficiency is around 10% and the frequency of trapping an active locus around 10%, it is appropriate to generate around 105 to 106 independent clones of cells. Since the mammalian genome includes approximately 105 genes, at least 90% of the genomic loci should be trapped, making it possible to monitor the activity of those genes. In drug screening assays, cells exposed to mutagens in the presence of the drug to be tested can thus be counterselected to yield cell clones having altered levels of gene expression that are due to the mutagenic effect. Statistical analysis is then performed to assess the efficacy and potency of a particular drug. The fewer clones of cells that are isolated during counter-selection, the fewer were the genes that underwent activity shifts, i.e. were mutated. Alternatively, in an assay to evaluate mutagen protectants, the fewer clones that grow during counter-selection, the better the protection.

The following non-limitative examples further describe and enable one of ordinary skill in the art to make and use the invention.

EXAMPLE 1

Construction of the Gene Trap Vector

All restriction digestions, ligations and other techniques related to the construction of this vector were carried out using standard molecular biology procedures.

Described are the detailed steps employed to construct the vector shown in FIG. 2. The trap vector reported in this example includes the herpes simplex virus thymidine kinase gene (HSV 106) (Mc Knight, 1980), the neomycin phosphotransferase gene (Neo), a splice acceptor consensus and stop codons, and was constructed as follows. For engineering of the positive-negative double selectable marker gene, Neo was derived from the pPNT plasmid (Tubulewics et al., Cell, 1990) by cutting with EcoRI and EagI and a 4.2 kb fragment was purified using Gene Clean (Bio 101). The other selectable marker gene, the HSV-TK was isolated from pPNT by cutting with Xma I and EcoRI and a 1.8 kb fragment was purified with Gene Clean. The TK and neo fragments were joined using the synthetic linker described under SEQ-ID with an Xma I site at the 5' end and EagI at the 3' end. The result and construct (termed PGK-TEO) is shown in FIG. 2 and gives rise to a fusion protein having both neomycin phosphotransferase and thymidine kinase activities. The fusion protein activities of the same levels as the individual proteins.

Next, a regulatory construct was prepared to include a PGK promoter, a functional splice acceptor consensus sequence, a universal stop sequence and a BiP internal ribosome entry site. These elements were joined together in that sequence from 5' to 3'. To achieve that trap construction, the PGK-TEO construct was cut with Sac I and Sal I including a portion of the TK fragment, the linker and the entire neo gene including the poly A-signal. An EcoRI site was introduced upstream of the TK-translation initiation site, just prior to the Kozak-sequence (Kozak 1986) to join that functional gene to the regulatory construct. This 470 bp fragment encodes the TK N-terminal region including the 5' EcoRI site and the 3' Sac I is generated by PCR amplification of HSV-TK clone. The resulting construct is a new cloning fragment of the TK-neo fusion protein that makes is possible to easily substitute promoters/alternative regulatory elements, now cloned in Bluescript KS+, at the SalI and EcoRI sites.

A splice acceptor consensus sequence, a stop sequence and a BiP IRES were also joined in a separate construction scheme as follows. The splice acceptor used was originally isolated from the genome of the Ad5 adenovirus. (Friedrich and Soriano, Genes Dev. 1991) The stop sequence was a 34 bp synthetic oligonucleotide having amber and ochre sequences in all three frames. The IRES element used derived from the gene encoding the immunoglobulin binding protein (BiP) (Macejak and Sarnow, 1991; Oh and Sarnow, 1993; Mc Bratney et al, 1993), and was a 220 bp fragment isolated from the pL7gCAT retroviral vector termed using the 5' PstI site and the 3' EcoR1 site. The splice acceptor consensus sequence was modified by introduction of novel Synthetic 115 bp oligonucleotides, that had BglII and XhoI sites at the 5' end and a Hind III site at the 3' end encoding STOP codons in all three reading frames. Then the IRES element was ligated to splice acceptor-STOP fragment in Bluescript KS+ using EcoRI and Bam HI sites to yield an insert size of 369 bp. The ligation of the Bam H1 to Bg1 II cohesive ends eliminates both those restriction sites.

The plasmid containing the regulatory sequences was digested with SalI and EcoRI, generating a linear fragment of 3.4 kb length including the plasmid backbone, for insertion of the functional gene encoding the selectable marker fusion protein Tk-neo. In a further aspect of the invention, the functional gene encoding TK-neo, size 2.3 kb is released from the plasmid using the restriction endonucleases SalI and EcoRI.

The linear fragment encoding, Tk-neo of size 2.3 kb is being ligated to the linearized plasmid containing the regulatory elements (SA-STOP-S) at the Sal I and Eco R1 sites. This results in an insert of total size of 2.8 kb which can be released and purified from the plasmid backbone for further studies using XhoI digestion.

EXAMPLE 2

Validation of Gene Trap Function

Attempt to demonstrate the function of the nucleic acid construct as a promoter/gene trap. The insert of the plasmid including the splice acceptor consensus sequence, the stop codon sequence, the IRES and the HSV-TK/Neo fusion protein coding sequence (hereafter termed SATEO), was cut out from the backbone plasmid, cleaned with phenol/chloroform, precipitated in 300 mM NH4Ac and 30% ethanol and air-dried. The SATEO construct was subsequently redissolved in TE (10 mM Tris-HCl pH 8.0 and 1 mM EDTA) under sterile conditions for electroporation into cultured ES cells, or other cell lines, including 3T3 or GP+E 86.

ES cells were trypsinized in 0.25% trypsin (Gibco) for 3 to 5 minutes at 37° C. subsequent to washing in PBS, then protease was quenched with three volumes of culture medium containing 15% FCS. The cell suspension was transferred into 15 ml conical culture tubes and spun for 5 minutes at 900 rpm (80 g) at room temperature in a Sorvall 6000D table top centrifuge. The cell-pellet was resuspended into PBS, Ca++, Mg++-free containing 20 µg/ml of DNA. Then, 300 µl of the cell suspension (107 cells/ml) was introduced into an electroporation cuvette of 0.4 cm electrode distance and electroporated with one pulse at 500 µF capacitance and a voltage of 250 V. Subsequent to the electroporation, cells were allowed to recover for 10 minutes prior to plating into either on 10 cm dish, or all 6 wells of a 6-well plate. Following culture for 24 hours, the medium was supplemented with 150 µg/ml of G418 for selection of cells expressing Neo. The transfected cells were maintained in culture under selective conditions for 7 days, then fixed, stained with trypan blue and the number of colonies counted.

The original plasmid including the SA-STOP-IRES fragment was linearized using the eight-cutter Not I, and was then used to generate an anti-sense probe to assay for correct usage of the splice acceptor junction. Using the T3 RNA-polymerase, 32P-labeled, 444 bp single stranded RNA was generated using the Riboprobe kit (Promega). Liquid hybridization of the riboprobe with RNA extracted from 5 clones of GP+E 86 cells selected following transfection with the gene trap was performed according to the protocol described by the kit manufacturer. Controls included: RNA from one clone of GP+E 86 cells transfected with ROSA-β gal; and RNA from untransfected ES cells and STO cells.

The protocol used was, in summary, as follows: RNA (20 µg) was dried, redissolved in 30 µl hybridization buffer together with 1 µl of Riboprobe (2.4×105 cpm) and incubated overnight at 45⁻C. The next morning, the hybridization reaction mixture was diluted with 350 µl RNase buffer (containing 2 µg/ml Range T1 and 40 µg/ml Range A) and incubated for 30 minutes at 37⁻C.

Subsequent to the Range digestion, samples were prepared for analysis using a 6% gel equivalent to those for DNA sequence analysis. Gel electrophoresis was performed for 5 hours at 65 Watts, and subsequently the gel was dried and exposed for autoradiography overnight at −70° C. using, Kodak XOM film. The autoradiograph is shown in FIG. 3.

EXAMPLE 3

Frequency of Trapping Active Loci

The experiments reported here were performed to calculate the frequency at which active chromosomal loci were trapped using the gene trap of the invention, compared to transfecting the selectable marker gene regulated by a heterologous promoter conferring constitutive and ubiquitous expression.

Numbers of colonies were counted and the ratios calculated of trapped loci divided by the number of colonies obtained from transfection of the plasmid which includes the constitutively expressed promoter. The numbers are shown in Table 2.

The vector of the invention is compared to gene traps previously reported (Friedrich and Soriano 1991) that yield relatively high frequencies of locus trapping including ROSA Bgeo. The vector ROSAβgal which includes a constitutively expressed neo gene was used as reference to calculate the trapping frequency of ROSAβgeo and the vector of the invention.

| Vectors | Cells | # colonies | # colonies trap | % Trap efficiency |
|---|---|---|---|---|
| ROSA βgal | GP+E86 | 304 | | |
| ROSA βgeo | GP+E86 | | 11 | 3.6% |
| pSATEO | GP+E86 | | 60 | 19.7% |
| pSATEO-Hyg | 3T3 | 93 | 26 | 27.9% |

Conclusion: The frequency of trapping active loci is improved by approximately one order of magnitude over other, previously reported vectors. This improvement is critical when attempting to screen the entire genome for regulated loci.

EXAMPLE 4

Construction of the Gene Trap Retrovirus

The hygromycin phosphotransferase (hyg) gene to be regulated by the 5'LTR of the retroviral vector was introduced in the construct so that the titer of virus producing cells could be determined. The hyg gene was isolated from the plasmid pCEP4 (Invitrogen) using PCR amplification and the restriction sites Pvu II at the 5'-end, XhoI and Cla I sites at the 3'-end. The resulting 1.1 kb PCR fragment was cloned into the retroviral vector pLNCX (Miller and Rosman, 1989) by blunt end ligation at the Pvu II site and cohesive end ligation at the Cla I site. The resulting vector was cut with Xho I for cloning of the 2.8 kb pSATEO fragment. That ligation yielded the desired vector containing the trap insert in both orientations with regard to direction of transcription from the 5'-LTR. To avoid interference of viral transcription with the trap function, vectors containing SATEO inserts oriented opposite to the 5'-LTR were analyzed and further pursued. See FIG. 4.

EXAMPLE 5

Virus-Producing Cell Lines/Titers

Gene trap retrovirus producing clones of cells were generated using the ecotropic producer cell line GP+E 86 (Markowitz et al.,1988) by electroporation. Confluent cultures of cells were trypsinized, washed and resuspended to a density of $10^7$ cells/ml in PBS containing vector DNA (20 µg/ml). DNA to be used for electroporation was first linearized with Ssp I, cleaned with phenol/chloroform, precipitated in ethanol, dried and redissolved in PBS. The cell-DNA mixture was transferred to a electroporation cuvette of 0.4 cm electrode distance, and electroporation is performed using one pulse of 500 µF and 400 V.

After 24 hours, hyg selection was started by supplementing the culture medium with 200 µg/ml of hygromycin. Colonies were identified after 7 to 10 days, when initially 75 colonies were picked and expanded for analysis of viral titers. Expansion was carried out in 48-well plates and then 6-well plates. Supernatant from confluent cultures in 6-well plates was first filtered through 0.45 µm filters and then frozen at −70° C. Viral titers of the frozen supernatant were assayed on NIH-3T3 cells using cultures at 30% confluency and polybrene detergent (8 µg/ml; Sigma).

Tenfold (10-2, 10-3, 10-4) serial dilutions of the virus supernatants were used for transduction experiments into NIH-3T3 cells by incubation for an initial period of 2 hours and diluted with standard culture medium. Selection in Hyg was initiated 24 hours following the transduction experiment. Hyg-resistant colonies were identified after 7 to 10 days when the cells were fixed in methanol and stained with Giemsa stain. Blue colonies were counted.

The results were, in summary, as follows: Out of 75 clones, 11 had a titer higher than $10^5$ cfu/ml, 49 clones had a titer between $10^4$ cfu/ml and $10^5$ cfu/ml, and 15 clones had titer of $10^3$ cfu/ml to $10^4$ cfu/ml. The clones with the highest titers ranged between $2 \times 10^5$ and $7 \times 10^5$ cfu/ml.

EXAMPLE 6

Transduction Efficiency

ES cells were plated at various densities ranging from $5 \times 10^2$ cells to $1 \times 10^5$ cells per well of a 6-well plate, which corresponded to a density of 500 cells/cm$^2$ to $10^4$ cells/cm$^2$.

The number of virus particles was held constant at $2 \times 10^5$ cfu/well, and thus, the multiplicity of infection for the various cell densities mentioned above ranges from 2 to 400, respectively. The protocol for viral transduction was identical to the one described above, and 24 hours following transduction, selection of cell clones for expression of neo from trapped active chromosomal loci was carried out by supplementing the culture medium with 150 µg/ml of G418. Selection in G418 was performed for 7 days when colonies were fixed, stained with Giemsa and counted. Detailed results of the transduction efficiency are illustrated in FIG. 5.

EXAMPLE 7

Selection for Regulated Genes in Embryonic Stem Cells

Upon Induction of Differentiation: Standard cultures of mouse ES cells were grown under conditions that maintained the undifferentiated phenotype, in the presence of differentiation inhibiting activity/leukemia inhibitory factor (DIA/LIF) or feeder cell layers (Robertson, 1987) A culture of ES cells was generally started by thawing a vial of frozen cells (106 cells/ml) and plating into 2 wells of a 6-well plate (coated with gelatin 0.1 mg/ml dilution of a 2% stock, Sigma, in PBS for 30 minutes) in standard ES cell medium consisting of DMEM, high glucose, supplemented with 15% fetal calf serum (Hyclone, defined or characterized), non-essential amino acids, β-mercaptoethanol, penicillinstreptomycin, and leukemia inhibitory factor (LIF, 1000 U/ml, ESGRO, Gibco-BRL). The medium was changed every day, and the cells were generally split every 2 days at a ratio of 1:8. Cells were maintained in the presence of LIF. ES cells were plated at a low density ($5 \times 10^3$ cells/well; 6-well plate) and incubated with viral supernatant (containing approximately $2 \times 105$ pfu) prior to transduction with the gene trap retrovirus. This yielded a multiplicity of infection of 40. At 24 hours after retroviral transduction, ES cells were cultured under drug selection for expression of the positive selectable marker, neomycin phosphotransferase. Selection of cells in G418 (125 to 175 µg/ml) yielded clones of drug resistant colonies after about 6 to 8 days. The yield has been approximately 900 colonies obtained from a transduction efficiency of around 30%, and a trap efficiency of 10 to 20%. Thus, the number of cells initially transduced was around $5 \times 104$ cells. At that time, the colonies were divided into sub-cultures, each consisting of 10 to 100 colonies. Colonies to be cultured in small pools disaggregated and plated at low density under conditions that allow for differentiation of the ES cells into various lineages, i.e., in the absence of LIF/DIA.

Subsequent to differentiation, after around 48 to 72 hours, cells were exposed to drugs for negative selection, i.e., cells that were still expressing the gene trap vector were selected against, whereas cells whose locus of integration regulating the gene trap vector has turned off survived that selection. Since these selections were performed in batches of relatively small numbers of colonies, the surviving cells within one dish or culture well resulted from only very few initial colonies. Ideally, colonies were treated individually following positive selection. That approach was not practical, however, since the number of colonies to be screened was very large: ideally the number of clones obtained following positive selection would between $5 \times 10^5$ and $10^6$, in order to assure that most active loci will have been trapped and given rise to independent clones of cells. Upon negative selection with gancyclovir, a lag of at least one week to 10 days was noted for surviving cells to form colonies.

Additional issues that have to be considered include the rate of proliferation of differentiated cells that can be dramatically slower than in undifferentiated ES cells. Also, the cells' sensitivity to drug resistance was somewhat altered, i.e., clones of cells that initially are selected in 150 µg/ml of G418 for positive selection, and 5 µg/ml of gancyclovir for negative selection following differentiation, were then replica-plated and subjected to renewed positive selection in increased concentrations of G418, i.e., 200 to 300 µg/ml. Since counter-selection was performed in a total of 48 wells, each of which contained approximately 20 colonies (total of 1000) of positively selected clones of cells, the number of clones surviving the negative selection following differentiation has been difficult to estimate. A total of 139 colonies were picked from 48 wells, but the number of independent clones can not be inferred from that. It is certain that at least 48 of the colonies were from independent clones, since the cells from the individual wells were not pooled at any time during the selection.

As discussed above, those cells were replica plated and subjected to renewed positive selection in G418 to ascertain that they became sensitive to G418 in response to the differentiation process. Of the wells that showed cells proliferating vigorously in the presence of negative selectable drug, gancyclovir, but not proliferating in the presence of G418. Of the initial 139 clones, 64 were selected based on morphological criteria and growth properties and were replica plated and selected in G418.

Renewed selection was performed in different concentrations of G418 including 200 µg/ml and 750 µg/ml. During this selection 30 of the original 139 colonies showed sensitivity to G418. Out of those 30 colonies, at least 7 scored as independent clones, based on the fact that they were initially isolated from different wells and culture plates. Northern analysis of total RNA isolated from 9 clones of differentiated ES cells that have acquired G418 sensitivity yield the result shown in FIG. 8: the positive clone #9 showed a strong signal after an 18 hour exposure, whereas no signal could be detected in clones that became Ganc resistant and G418 sensitive following differentiation. Following exposure for 7 days, 3 lanes showed weak signals whereas the 6 remaining lanes were still blank. Several of these clones have been analyzed for presence of the trap provirus in the DNA using PCR. Except for one clone, C27, the analyzed clones are positive for provirus.

These data provide indirect evidence that several of the analyzed clones have down-regulated the locus of trap integration due to differentiation.

Clones E6 and C27 were further analyzed for chromosomal locus of trap integration. Prior to a detailed molecular analysis and identification of the trapped genetic loci in those cells, DNA was extracted and subjected to Southern analysis to assess the number of potential proviruses integrated in the genome. That analysis revealed that clone E6 has 2 independent copies of the proviruses and clone C27 contains one integrated provirus. That information was essential to evaluate if further analysis was justified.

Several strategies are being pursued to isolate the genes that correspond to the locus of trap integration. The approach described above that aims at the selection of genes turned off during differentiation requires for analysis of genomic DNA. In contrast, if genes that are turned on are analyzed, RNA can directly be used to identify the corresponding gene. Thus, the former one includes the generation of limited genomic libraries in cosmids of large fragment including the chromosomal locus of trap integration. DNA is then isolated from the those cosmids and transfected into undifferentiated ES cans for stable transformation. Subsequent to transfection ES cells are selected in G418. Resistant clones can then be grown, RNA isolated, and sequences corresponding to the genomic locus identified using RACE-PCR, as described in the literature (Frohrnan,1990)

Cited Literature

1. McGinnis, W. and Krumlauf, R. 1992 Cell 68, 283–302
2. Krunlauf, R., 1992, Ann. Rev. Cell Biol. 8, 227–256
3. Malicki, Schughart and McGinnis, 1990, Cell 63, 961–967
4. Hunter, T. 1991, Cell 64, 249–270
5. Varmus, H. 1984, Ann. Rev. Genet. 18, 553–612
6. Fowell, D. 1991, ImInunol. Rev. 123, 37–59
7. Watanabe-Fukunaga, R. et al. 1992 Nature 356, 314–317
8. Young, .1991, Ann. Rev. Biochem. 60, 689–715
9. Brown, D. 1984, Cell 37,359–365
10. Sharp, P., 1987, Science 235, 766–771
11. Weiner, A., 1993, Cell 72, 161–164
12. Padgett, R. A., Grabowski, P. J., Konarska, M. M. and Sharp, P., 1985, Trends Biochem Sci. 10, 154–157
13 Flanagan, J., Chan, D., and Leder, P 1991, Cell 64, 1025–1035
14. Guthrie, C. 1991, Science 253, 766–771
15. Sulston et al. 1992, Nature 356, 37–41
16. Casadaban, M. J. and Cohen, S. N. 1980, PNAS 76, 4530–4533
17. Chu, G. and Sharp, P. 1981, Nature 289, 378–382
18. Weber, D. M., de Villier, J. and Schaffner, W., 1984 Cell 36, 983–992
19. DeGregori J. Russ A. von Melchner H. Rayburn H. Priyaranjan P. Jenkins NA. Copeland NG. Ruley HE. 1994 Genes Dev. 8:265–76
20. Hill DP. Wurst W. 1993, Methods in Enzymology. 225:664–81
21. Niwa H. Araki K. Kimura S. Taniguchi S. Wakasugi S. Yamamura K., 1993, Journal of Biochemistry. 113(3):343–9
22. Chang W. Hubbard SC. Friedel C. Ruley HE., 1993, Virology. 193(2):737–47
23. Joyner AL. Auerbach A. Skarnes WC., 1992 Ciba Foundation Symposium. 165:277–88
24. Skarnes WC. Auerbach BA. Joyner AL., 1992, Genes Dev 6(6):903–18
25. Joyner AL., 1991, Bioessays. 13(12):649–56
26. Reddy S. Rayburn H. von Melchner H. Ruley HE. 1992, Proc. Natl. Acad. Sci.USA 89(15):6721–5
27. Macleod D. Lovell-Badge R. Jones S. Jackson I. 1991, Nucleic Acids Research. 19(1):17–23
28. Reddy S. DeGregori JV. von Melchner H. Ruley HE. 1991, J. Virology. 65(3):1507–15
29. von Melchner H. Reddy S. Ruley HE. 1990, Proc.Natl Acad Sci USA 87(10):3733–7
30. Gossler,A., Joyner, A., Rossant, J. and Skarnes, W. 1989, Science 244, 463–465
31. Friedrich G. and Soriano, P. 1991, Genes & Dev. 5, 1513–1523
32. vonMelchner, H., DeGregori, J. V., Rayburn,H., Reddy, S., Friedel, C. and Ruley, H. E. 1992, Genes & Dev., 5, 919–927
33. Soriano,P., Friedrich, G., Lawinger, P., 1991, J. Virol. 65, 2314–2319
34. Miller, A. D. and Rosman, G. J. 1989, Biotechniques, 7, 980–990
35. Robertson E. J., 1986, Trends in Genetics 2, 9–13
36. Thayer, M. J., Tabscott, S. J., Davis, R. L., Wright, W. E., Lassar, A. B. and Weintraub, H., 1989, Cell 58, 241–248
37. Bishop, M. 1983, Ann. Rev. Biochem. 52, 301–354
38. Mc Knight, S. L. 1980, Nucleic Acids Res. 8, 5949–5964
39. Tubulewics, V. L. J., Crawford, C. E., Jackson, P. K., Bronson, R. T., and Mulligan, R. C. 1991, Cell 65, 1153–1163
40. Kosak, M. 1986, Cell 44, 283–292
41. Macejak DG. Sarnow P., Nature. 353, 90–94, 1991
42. Oh SK. Sarnow P 1993, Current Opinion in Genetics & Development. 3, 295–300
43 McBratney S. Chen CY. Sarnow P., 1993 Current Opinion in Cell Biology 5, 961–965
44. Markowitz, D., Goff, S. and Banks, A, 1988, J.Virol. 62, 1120–1124
45. Robertson, E. J. 1987 in Teratocarcinomas and Embryonic Stem Cells: A Practical Approach, 71–112, IRL Press, Oxford
46. Adams MD. Soares MB. Kerlavage AR. Fields C. Venter JC. Nature Genetics 1993, 4 :373–380
47. Venter JC, 1993 Journal of Pharmacy & Pharmacology. 45 Suppl 1:355–60
48. Hentze MW. Argos P. 1991, Nucleic Acids Research. 19(8):1739–40
49. Frohman, M. A., Dush, M. K., and Martin, G. R., 1988, Proc Natl. Acad. Sci. USA 85, 8998–9002
50. Schraml P. Shipman R. Stulz P. Ludwig CU., 1993 Trends in Genetics 9(3):70–1
51. Rosenberg M. Przybylska M. Straus D. 1994, Proc Natl Acad. Sci USA 91(13):6113–7
52. Sturzl M. Roth WK. 1990 Trends in Genetics. 6(4): 106.
53. Fargnoli J. Holbrook NJ. Fornace AJ Jr. 1990 Analytical Biochemistry. 187(2):364–73
54. Liang P. Pardee AB. 1992 Science. 257(5072):967–71
55. Liang P. Averboukh L. Pardee AB. 1993 Nucleic Acids Research. 21(14):3269–75
56. Mitchelson A., Simonelig M., Williams C., O'Hare K. 1993 Genes Dev. 7(2):241–9
57. Elela SA. Nazar RN. 1992 Biochimica et Biophysica Acta. 1130(3):339–42.
58. Richter,J., 1993, Dev. Genetics 14,407–411
59. Sambrook,J., Fritsch, E .F., and Maniatis,T., 1989, Molecular Cloning:A Laboratory Manual; Cold Spring Harbor Laboratory Press

What is claimed is:

1. A nucleic acid construct comprising in downstream sequence (i) a cassette having a functional splice acceptor, a translation stop sequence and an internal ribosome entry site and (ii) a promoterless protein coding sequence encoding one polypeptide providing both positive and negative selection traits.

2. The nucleic acid construct of claim 1 wherein the functional splice acceptor is a splice acceptor consensus sequence.

3. The nucleic acid construct of claim 1 wherein the internal ribosome entry site is a mammalian internal ribosome entry site.

4. The nucleic acid construct of claim 4 wherein the mammalian internal ribosome entry site is an immunoglobulin heavy chain binding protein internal ribosome entry site.

5. The nucleic acid construct of claim 1 wherein the internal ribosome entry site is a picornavirus internal ribosome entry site.

6. The nucleic acid construct of claim 5 wherein the picornavirus internal ribosome entry site is selected from the group consisting of an encephalomyocarditis virus or polio virus internal ribosome entry site.

7. The nucleic acid construct of claim 1 wherein the promoterless protein coding sequence encodes a single protein whose expression and non-expression can be detected as positive and negative selection traits, respectively.

8. The nucleic acid construct of claim 7 wherein the single protein so encoded is selected from the group consisting of hypoxanthine guanine phosphoribosyl transferase(HGPRT) and β-galactosidase.

9. The nucleic acid construct of claim 1 wherein the promoterless protein coding sequence encodes a fusion protein having first and second polynucleotide sequences whose expression can be detected as positive and negative selection traits, respectively.

10. The nucleic acid construct of claim 9 wherein the first polypeptide sequence is selected from the group consisting of a functional neomycin phosphotransferase and a functional hygromycin.

11. The nucleic acid construct of claim 9 wherein the second polypeptide sequence is a thymidine kinase.

12. The nucleic acid construct of claim 1 wherein the promoterless protein coding sequence comprises operably linked first and second nucleic acid sequences encoding separate proteins respectively providing positive and negative selection traits and an internal ribosome entry site therebetween.

13. The nucleic acid construct of claim 1 wherein the promoterless protein coding sequence includes a translation stop sequence, and which further comprises a functional splice donor sequence downstream therefrom, but lacks a polyadenylation signal in cis downstream of the promoterless protein coding sequence.

14. A viral vector incorporated with the nucleic acid construct of claim 1, wherein the viral vector does not contain a promoter positioned or configured such that the promoter regulates the expression of the promoterless protein coding sequence.

15. The viral vector of claim 14 which is derived from a retrovirus.

16. The retrovirus-derived vector of claim 15 which comprises in downstream sequence (a) an integration sequence and (b) a nucleic acid construct comprising in downstream sequence (i) a casette having a functional splice acceptor, a translation stop sequence and an internal ribosome entry site and (ii) a promoterless protein coding sequence and encoding at least one polypeptide providing positive and a negative selection traits.

17. The retrovirus-derived vector of claim 16 wherein the functional splice acceptor is a splice acceptor consensus sequence.

18. The retrovirus-derived vector of claim 16 wherein the internal ribosome entry site is selected from the group consisting of a mammalian internal ribosome entry site and a picornaviral internal ribosome entry site.

19. The retrovirus-derived vector of claim 15 which comprises in downstream sequence (a) an integration sequence and (b) a nucleic acid construct comprising in downstream sequence (i) a cassette having a functional splice acceptor, a translation stop sequence and an internal ribosome entry site and (ii) a promoterless protein coding sequence which comprises operably linked first and second nucleic acid sequences encoding separate proteins respectively providing positive and negative selection traits and an internal ribosome entry site therebetween.

20. The retrovirus-derived vector of claim 19 wherein the functional splice acceptor is a splice acceptor consensus sequence.

21. The retrovirus-derived vector of claim 19 wherein the internal ribosome entry site is selected from the group consisting of a mammalian internal ribosome entry site and a picornaviral internal ribosome entry site.

22. The retrovirus-derived vector of claim 15 which comprises in downstream sequence (a) an integration sequence and (b) a nucleic acid construct comprising in downstream sequence (i) a cassette having a functional splice acceptor, a translation stop sequence and an internal ribosome entry site and (ii) a promoterless protein coding sequence that encodes at least one polypeptide providing positive and negative selection traits and includes a translation stop sequence, and (iii) a functional splice donor sequence, and which lacks a polyadenylation signal is cis.

23. The retrovirus-derived vector of claim 22 wherein the functional splice acceptor is a splice acceptor consensus sequence.

24. The retrovirus-derived vector of claim 22 wherein the internal ribosome entry site is selected from the group consisting of a mammalian internal ribosome entry site and a picornaviral internal ribosome entry site.

25. A eukaryotic cell into which has been integrated the vector of claim 14.

26. The eukaryotic cell of claim 25 which is a pluripotent cell.

27. The eukaryotic cell of claim 26 which is a stem cell.

28. The eukaryotic cell of claim 27 which is an embryonic stem cell.

29. A eukaryotic cell into which has been integrated the vector of claim 15.

30. A method for selecting a cell in which an activity is regulated upon a cellular transition event, which method comprises (i) introducing the viral vector of claim 14 into a cell downstream from an inactive promoter which becomes active upon occurence of the cellular transition event:

(ii) selecting for an inactive genetic locus in said cell prior to the cellular transition event: and (iii) selecting for an active genetic locus in said cell after the cellular transition event.

31. A method for selecting a cell in which an activity is regulated upon a cellular transition event, which method comprises (i) introducing the viral vector of claim 14 into a cell downstream from an active promoter which becomes inactive upon said cellular transition event;

(ii) selecting for an active genetic locus in said cell prior to the cellular transition event; and (iii) selecting for an inactive genetic locus in said cell after the cellular transition event.

* * * * *